(12) United States Patent
Perlstein et al.

(10) Patent No.: US 10,166,236 B2
(45) Date of Patent: Jan. 1, 2019

(54) PHARMACEUTICAL FORMULATIONS COMPRISING SUBSTITUTED PYRAZOLO [5,1-C]PYRIDO[4,3-E][1,2,4]TRIAZINES FOR TREATING LYSOSOMAL STORAGE DISORDERS

(71) Applicant: Perlara PBC, South San Francisco, CA (US)

(72) Inventors: Ethan Oren Perlstein, San Francisco, CA (US); Nina Di Primio, San Francisco, CA (US); Tom Aaron Hartl, San Francisco, CA (US); Sangeetha Venkatraman Iyer, San Francisco, CA (US); Alexander James Ludin, San Francisco, CA (US); Tamy May Sharly Portillo Rodriguez, San Francisco, CA (US); John Alan Tucker, San Francisco, CA (US)

(73) Assignee: Perlara PBC, South San Francisco, CA (US)

( * ) Notice: Subject to any disclaimer, the term of this patent is extended or adjusted under 35 U.S.C. 154(b) by 0 days.

(21) Appl. No.: 15/464,214

(22) Filed: Mar. 20, 2017

(65) Prior Publication Data

US 2017/0281635 A1 Oct. 5, 2017

Related U.S. Application Data

(60) Provisional application No. 62/311,164, filed on Mar. 21, 2016.

(51) Int. Cl.
| | |
|---|---|
| *A61K 31/4353* | (2006.01) |
| *A61K 31/53* | (2006.01) |
| *A61K 31/724* | (2006.01) |
| *A61K 31/519* | (2006.01) |
| *A61K 31/5377* | (2006.01) |

(52) U.S. Cl.
CPC ............ *A61K 31/53* (2013.01); *A61K 31/519* (2013.01); *A61K 31/5377* (2013.01); *A61K 31/724* (2013.01)

(58) Field of Classification Search
CPC .................................................. A61K 31/4353
USPC ........................................................ 514/294
See application file for complete search history.

(56) References Cited

U.S. PATENT DOCUMENTS

| | | |
|---|---|---|
| 2009/0143367 A1 | 6/2009 | Malamas et al. |
| 2012/0302564 A1 | 11/2012 | Lankau et al. |
| 2014/0147386 A1 | 5/2014 | Andres-Gil et al. |

FOREIGN PATENT DOCUMENTS

| | | |
|---|---|---|
| WO | WO-2010/138833 | 12/2010 |
| WO | WO-2015/061280 | 4/2015 |
| WO | WO 17/165311 | * 9/2017 |

OTHER PUBLICATIONS

Jordan, V. C. Nature Reviews: Drug Discovery, 2, 2003, 205.*
Hackam, et al. JAMA, 296(14), 2006, 1731-1732.*
International Search Report and Written Opinion for PCT/US2017/023244 dated Jul. 27, 2017, 11 pages.
Pubmed CID 45590262, "MolPort-008-138-151", US National Library of Medicine, 2010, https://pubchem.ncbi.nlm.nih.gov/compound/455902762, p. 3.
Pubmed CID 45590274, "MolPort-008-138-527", US National Library of Medicine, 2010, https://pubchem.ncbi.nlm.nih.gov/compound/45590274, p. 3.
Lachmann et al., "Treatment with mislugstat reverses the lipid-trafficking defect in Niemann-Pick disease type C," Neurobiology of Disease, 16 (2004), 654-658.
Ikonen et al., "Cellular pathology of Niemann-Pick type C disease," 15 (2004), 445-454.
Harzer et al., "Concurrent increase of cholesterol, sphinomyelin and glucosylceramide in the spleen from non-neurologic Niemann-Pick type C patients but also patients possibly affected with other lipid trafficking disorders," FEBS Letters 537 (2003), 177-181.

* cited by examiner

*Primary Examiner* — Douglas M Willis
(74) *Attorney, Agent, or Firm* — Sheppard Mullin Richter & Hampton LLP

(57) ABSTRACT

This disclosure provides compounds, such as compounds of Formula I:

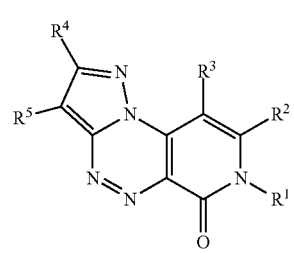

pharmaceutical formulations thereof, and related methods of use for the treatment of defects of cholesterol homeostasis including lysosomal storage disorders such as Niemann-Pick Type C disease.

3 Claims, 7 Drawing Sheets

PHARMACEUTICAL FORMULATIONS COMPRISING SUBSTITUTED PYRAZOLO[5,1-C]PYRIDO[4,3-E][1,2,4]TRIAZINES FOR TREATING LYSOSOMAL STORAGE DISORDERS

CROSS REFERENCE TO RELATED APPLICATIONS

This application claims the benefit under 35 U.S.C. § 119(e) to U.S. Provisional Application Ser. No. 62/311,164, filed on Mar. 21, 2016, which is hereby incorporated by reference in its entirety.

FIELD

The present disclosure provides fused heterocyclic organic compounds, compositions containing such compounds, medical kits, and methods for using such compounds and compositions for the treatment of Niemann-Pick Type C and related genetic disorders.

BACKGROUND

Niemann-Pick Type C (NPC) disease is a lethal inherited neurovisceral lysosomal storage disorder caused primarily by recessive mutations in the NPC1 gene. NPC disease is characterized physiologically in humans, and in animals broadly, by defects in cellular cholesterol homeostasis leading to defects in autophagy. Specifically, unesterified cholesterol derived from the low-density lipoprotein (LDL) pathway is taken up by cells but unable to be assimilated metabolically because cholesterol-laden compartments are unable to fuse with lysosomes, resulting in reduced catabolism and a state of cholesterol limitation. Some cell types and tissues are hypersensitive to cholesterol limitation or disruption of autophagic flux, as well as to secondary accumulations of other cellular lipids such as sphingomyelin. Additional pathophysiologic complexity arises because cholesterol is the precursor for essential metabolites that include steroid hormones, oxysterols, bile acids and cell membrane itself. Brain, liver, spleen and lung are among the organs that manifest pathophysiology in NPC patients. Although clinical presentation and time of disease onset varies from patient to patient, NPC disease ultimately leads to premature death in young adulthood by a progressive neurodegenerative decline.

Multiple animal models of NPC disease are possible because the NPC1 gene is evolutionarily ancient and conserved throughout the Animal Kingdom. The genomes of baker's yeast (*Saccharomyces cerevisiae*), nematodes (*Caenorhabditis elegans*), fruit flies (*Drosophila melanogaster*), zebrafish (*Danio rerio*) and mice (*Mus musculus*) all have an ancestral version of the NPC1 gene. Cholesterol limitation is observed across multiple species. NPC disease models have been generated and studied in nematodes, fruit flies, zebrafish and mice. Nematodes lacking the NPC1 gene are hypersensitive to cholesterol restriction, fail to reach adulthood with normal timing, and produce smaller broods because specific cells have defects in autophagic flux, resulting in the inability to convert cholesterol to an essential hormone called dafachronic acid. Similarly, fruit flies lacking the NPC1 gene usually die as early-stage larvae due to the inability of specific cells to convert cholesterol to an essential hormone called ecdysone. Fruit flies that survive into adulthood exhibit neurodegeneration and other disease-relevant phenotypes. Mice lacking the NPC1 gene die prematurely due to neurological decline and rapid weight loss, with multiple cell types exhibiting phenotypes of cholesterol limitation.

There is no FDA approved treatment for NPC. Current experimental drugs for NPC are being repurposed and were discovered on the basis of normalization of a cellular phenotype in patient-derived fibroblasts, namely clearance of LDL-derived cholesterol storage. However, cells derived from NPC patients with certain mutations do not exhibit the cholesterol storage phenotype, demonstrating that while this storage phenotype is diagnostic of disease it is not the means to reversing disease. The compounds described herein were discovered first in a whole animal, then validated in a patient cell model, and then further validated in a mouse model, resulting in compounds that reverse the root causes of disease via a bypass pathway rather than by reversing a cellular phenotype that may simply be a feature of disease.

SUMMARY

It is contemplated that compounds of Formulas I-IV enable cells and animals to bypass the loss of NPC1 gene function, thereby alleviating the root physiological defects caused by an NPC1 gene mutation. The present disclosure generally provides fused heterocyclic organic compounds and pharmaceutically acceptable salts thereof, compositions and pharmaceutical formulations containing such compounds, medical kits, and methods for using such compounds, compositions, and formulations for the treatment of lysosomal storage disorders including, for example, Niemann-Pick Type C, and/or for modulating cholesterol homeostasis.

One aspect of the present disclosure provides a family of fused heterotricyclic organic compounds of Formula I:

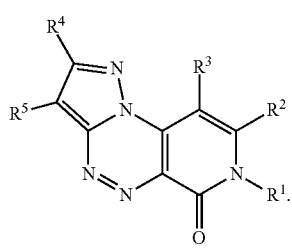

Another aspect of the present disclosure provides a family of fused heterotricyclic organic compounds of Formula II:

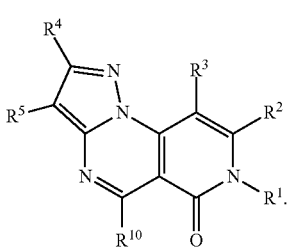

Another aspect of the present disclosure provides a family of fused heterotricyclic organic compounds of Formula III:

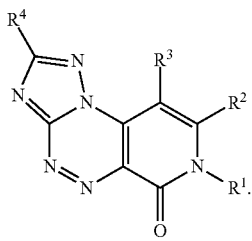

III

Another aspect of the present disclosure provides a family of fused heterotricyclic organic compounds of Formula IV:

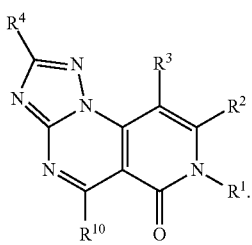

IV

The variable groups for Formulas I-IV are provided below.

For each of Formulas I-IV, the present disclosure provides the compounds, pharmaceutically acceptable salts thereof, and pharmaceutical formulations containing either the compound or a pharmaceutically acceptable salt thereof.

In some embodiments, the pharmaceutical formulations also comprise cyclodextrin.

Another aspect of the present disclosure provides methods of treatment of a lysosomal storage disorder by administering a therapeutically effective amount of a compound of Formulas I-IV or a pharmaceutically acceptable salt thereof. In some embodiments, the lysosomal storage disorder is Niemann-Pick Types A, B, & C, Batten disease, Wolman disease, Griscelli Type 1, Griscelli Type 2, Griscelli Type 3, Salla disease, cystinosis, Fabry disease, Gaucher Type 1, Gaucher Type 2, Sandhoff disease, alpha-mannosidosis, beta-mannosidosis, Ceroid lipofuscinosis, Aspartylglucosaminuria, mucopolysaccharidosis (MPS) Type 1, MPS Type 2, MPS Type 3A, MPS Type 3B, MPS Type 3C, MPS Type 3D, MPS Type IVB, MPS Type VI, MPC Type VII, Schindler disease, Metachromatic leukodystrophy 1, Metachromatic leukodystrophy 2, Tay-Sachs, Sialidosis, Morquio A, Fucosidosis, Pompe disease, Chediak-Higashi, Mucolipidosis 4, GM2 gangliosidosis, Pycnodystostosis, Globoid cell leukodystrophy, Pseudo-Hurler polydystrophy, Ceroid lipofuscinosis 2, Ceroid lipofuscinosis 6, or Ceroid lipofuscinosis 8.

In another aspect of the present disclosure provides methods of treatment for dyslipidemia by administering a therapeutically effective amount of a compound of Formulas I-IV or a pharmaceutically acceptable salt thereof. In some embodiments, the dyslipidemia is Familial hypercholesterolemia, Lysosomal acid lipase deficiency, Lathosterolosis, Desmosterolosis, CHILD syndrome, Smith-Lemli-Optiz Syndrome, or Tangier disease. Optionally, the method further includes administering a therapeutically effective amount of cyclodextrin to the patient.

BRIEF DESCRIPTION OF THE DRAWINGS

FIG. 1A) or 10 μM of either Compound 1 (FIG. 1B), a representative compound from the Formula I series, or U18666A (FIG. 1C).

DETAILED DESCRIPTION

I. Definitions

Figure 1:
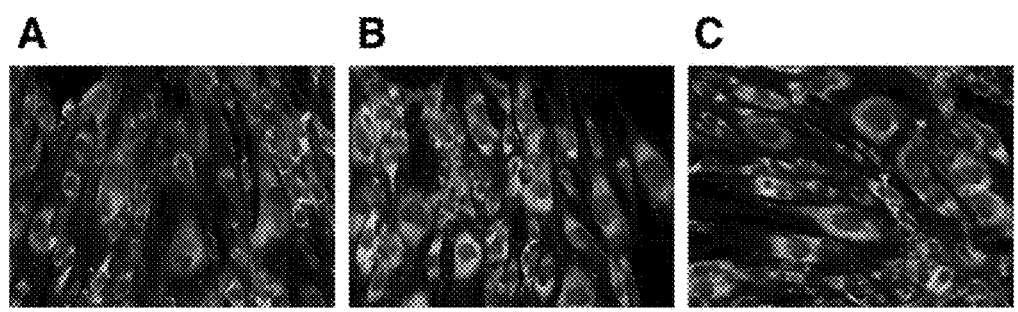
FIG. 1 is a series of photomicrographs showing the binding of filipin to cholesterol in an NPC patient fibroblast cell line that was treated for 48 hours with DMSO (vehicle control.

To facilitate an understanding of the present disclosure, a number of terms and phrases are defined below.

The terms "a" and "an" as used herein mean "one or more" and include the plural unless the context is inappropriate.

The term "alkyl" as used herein refers to a saturated straight or branched hydrocarbon, such as a straight or branched group of 1-12, 1-10, or 1-6 carbon atoms, referred to herein as $C_1$-$C_{12}$alkyl, $C_1$-$C_{10}$alkyl, and $C_1$-$C_6$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkylidene" refers to a divalent alkyl group. An exemplary alkylidene group is —$CH_2CH_2$—.

The term "haloalkyl" refers to an alkyl group that is substituted with at least one halogen. For example, —$CH_2F$, —$CHF_2$, —$CF_3$, —$CH_2CF_3$, —$CF_2CF_3$, and the like.

The term "cycloalkyl" refers to a monovalent saturated cyclic, bicyclic, or bridged cyclic (e.g., adamantyl) hydrocarbon group of 3-12, 3-8, 4-8, or 4-6 carbons. Exemplary cycloalkyl groups include, but are not limited to, cyclohexanes, cyclopentanes, cyclobutanes and cyclopropanes. Unless specified otherwise, cycloalkyl groups are optionally substituted at one or more ring positions with halogen, alkoxy, or alkyl. In certain embodiments, the cycloalkyl group is not substituted, i.e., it is unsubstituted.

The term "aryl" is art-recognized and refers to a carbocyclic aromatic group. Representative aryl groups include phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "aryl" also includes polycyclic ring systems having two or more carbocyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, and/or aryls. In certain embodiments, the aromatic ring is substituted at one or more ring positions with halogen, alkyl, hydroxyl, or alkoxyl. In certain other embodiments, the aromatic ring is not substituted, i.e., it is unsubstituted.

The term "aralkyl" or "arylalkyl" refers to an alkyl group substituted with an aryl group.

The term "heteroaryl" is art-recognized and refers to aromatic groups that include at least one ring heteroatom. In certain instances, a heteroaryl group contains 1, 2, 3, or 4 ring heteroatoms. Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "heteroaryl" also includes polycyclic ring systems having two or more rings in which two or more carbons are common to two adjoining rings (the rings are "fused rings") wherein at least one of the rings is heteroaromatic, e.g., the other cyclic rings may be cycloalkyls, cycloalkenyls, cycloalkynyls, and/or aryls. In certain embodiments, the heteroaryl ring is substituted at one or more ring positions with halogen, alkyl, hydroxyl, or alkoxyl. In certain other embodiments, the heteroaryl ring is not substituted, i.e., it is unsubstituted.

The term "heteroaralkyl" refers to an alkyl group substituted with a heteroaryl group.

The terms "heterocyclyl" and "heterocyclic group" are art-recognized and refer to saturated or partially unsaturated 3- to 10-membered ring structures, alternatively 3- to 7-membered rings, whose ring structures include one to four heteroatoms, such as nitrogen, oxygen, and sulfur, but wherein the heteroatoms never make up more than half of the ring atoms. One example of a C$_3$ heterocyclyl is aziridinyl. Heterocycles also may be mono-, bi-, or other multicyclic ring systems. A heterocycle may be fused to one or more aryl, partially unsaturated, or saturated rings. Heterocyclyl groups include, for example, biotinyl, chromenyl, dihydrofuryl, dihydroindolyl, dihydropyranyl, dihydrothienyl, dithiazolyl, homopiperidinyl, imidazolidinyl, isoquinolyl, isothiazolidinyl, isoxazolidinyl, morpholinyl, oxolanyl, oxazolidinyl, phenoxanthenyl, piperazinyl, piperidinyl, pyranyl, pyrazolidinyl, pyrazolinyl, pyridyl, pyrimidinyl, pyrrolidinyl, pyrrolidin-2-onyl, pyrrolinyl, tetrahydrofuryl, tetrahydroisoquinolyl, tetrahydropyranyl, tetrahydroquinolyl, thiazolidinyl, thiolanyl, thiomorpholinyl, thiopyranyl, xanthenyl, lactones, lactams such as azetidinones and pyrrolidinones, sultams, sultones, and the like. Unless specified otherwise, the heterocyclic ring is optionally substituted at one or more positions with substituents such as alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. In certain embodiments, the heterocyclcyl group is not substituted, i.e., it is unsubstituted.

The term "heterocycloalkyl" is art-recognized and refers to a saturated heterocyclyl group as defined above.

The terms "amine" and "amino" are art-recognized and refer to both unsubstituted and substituted amines, e.g., a moiety represented by the general formula-N($R^{50}$)($R^{51}$), wherein $R^{50}$ and $R^{51}$ each independently represent hydrogen, alkyl, cycloalkyl, heterocyclyl, alkenyl, aryl, or aralkyl; or $R^{50}$ and $R^{51}$, taken together with the N atom to which they are attached complete a heterocycle having from 4 to 8 atoms in the ring structure. In certain embodiments, $R^{50}$ and $R^{51}$ each independently represent hydrogen, alkyl or alkenyl.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like.

The term "aryloxy" refers to —O-aryl, wherein aryl is as defined herein.

The term "carbamate" as used herein refers to a radical of the form —$R^g$OC(O)N($R^h$)—, —$R^g$OC(O)N($R^h$)$R^i$—, or —OC(O)N$R^h R^i$, wherein $R^g$, $R^h$ and $R^i$ are each independently alkoxy, aryloxy, alkyl, alkenyl, alkynyl, amide, amino, aryl, arylalkyl, carboxy, cyano, cycloalkyl, ester, ether, formyl, halogen, haloalkyl, heteroaryl, heterocyclyl, hydroxyl, ketone, nitro, sulfide, sulfonyl, or sulfonamide.

The term "carbonyl" refers to =O.

The term "carboxyl" or "carboxylic acid" refers to —C(O)OH.

The term "ketone" refers to —C(O)$R^x$, where $R^x$ is alkyl, cycloalkyl, heterocyclyl, aryl, heteroalkyl, or heteroaryl; each of which may be optionally substituted, as defined herein. "Alkanoyl" refers to —C(O)-alkyl.

The term "formyl" refers to C(O)H. The term "aldehyde" refers to the group —C(O)H.

The term "ester" refers to both —OC(O)R and —C(O)OR, wherein R is hydrogen, alkyl, cycloalkyl, heterocyclyl, aryl, heteroalkyl, or heteroaryl; each of which may be optionally substituted, as defined herein.

The term "carbonate group refers to —OC(O)$R^v$, where $R^v$ is alkyl, alkenyl, alkynyl, aryl, aralkyl, cycloalkyl, haloalkyl, or heterocycloalkyl group as described above.

The term "ether" refers to $R^u$(O)$R^w$, where $R^u$ and $R^w$ is independently, an alkyl, alkenyl, alkynyl, aryl, aralkyl, cycloalkyl, haloalkyl, or heterocycloalkyl group described above.

The term "amide" or "amido" as used herein refers to a radical of the form —R$^a$C(O)N(R$^b$)—, —R$^a$C(O)N(R$^b$)R$^c$, —C(O)NR$^b$R$^c$, or —C(O)NH$_2$, wherein R$^a$, R$^b$ and R$^c$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro. The amide can be attached to another group through the carbon, the nitrogen, R$^b$, R$^c$, or R$^a$. The amide also may be cyclic, for example R$^b$ and R$^c$, R$^a$ and R$^b$, or R$^a$ and R$^c$ may be joined to form a 3- to 12-membered ring, such as a 3- to 10-membered ring or a 5- to 6-membered ring.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$ alkenyl, $C_2$-$C_{10}$ alkenyl, and $C_2$-$C_6$ alkenyl, respectively. Exemplary alkenyl groups include vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, and the like.

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e. $C_{2-6}$ alkynyl), or 2 to 4 carbon atoms $C_{2-4}$ alkynyl). The term "alkynyl" also includes those groups having one triple bond and one double bond.

"Azide" or "azido" refers to —N$_3$.

"Cyano" refers to the group —CN.

The term "halogen" or "halo" includes fluoro, chloro, bromo, and iodo.

The term "hydroxy" or "hydroxyl" refers to the group —OH.

"Nitro" refers to the group —NO$_2$.

The term "sulfonamide" or "sulfonamido" as used herein refers to a radical having the structure —N(R$^r$)—SO$_2$—R$^s$— or —SO$_2$—N(R$^r$)R$^s$, where R$^r$, and R$^s$ can be, for example, hydrogen, alkyl, aryl, cycloalkyl, and heterocyclyl. Exemplary sulfonamides include alkylsulfonamides (e.g., where R$^s$ is alkyl), arylsulfonamides (e.g., where R$^s$ is aryl), cycloalkyl sulfonamides (e.g., where R$^s$ is cycloalkyl), and heterocyclyl sulfonamides (e.g., where R$^s$ is heterocyclyl), etc.

The term "sulfhydryl" refers to the group —SH.

"Sulfate" refers to SO$_4^{2-}$.

"Sulfonyl" refers to the group —S(O)$_2$R$^y$, where R$^y$ is alkyl, haloalkyl, heterocyclyl, cycloalkyl, heteroaryl, or aryl. Examples of sulfonyl are methylsulfonyl, ethylsulfonyl, phenylsulfonyl, and toluenesulfonyl.

"Alkylthio" refers to the group "alkyl-S—".

"Thiocarbonyl" refers to —C(=S).

"Sulfide" refers to —S—.

"Imino" refers to a group —C(NR$^z$)R$^z$, wherein each R$^z$ is independently selected from alkyl, cycloalkyl, heterocyclyl, aryl, and heteroaryl, each of which may be optionally substituted as described herein.

"Amidino" refers to —C(NH)(NH$_2$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is H, alkyl, aryl, cycloalkyl, heteroalkyl, heteroaryl or heterocyclyl, each of which may be optionally substituted. Examples of heteroalkyl groups include —OCH$_3$, —CH$_2$OCH$_3$, —SCH$_3$, —CH$_2$SCH$_3$, —NRCH$_3$, and —CH$_2$NRCH$_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Phosphate" refers to PO$_4^{3-}$. The term "phosphonato" refers to —P(O)(OR$^q$)$_2$, where R$^q$ is H, alkyl, alkenyl, alkynyl, aryl, arylalkyl, cycloalkyl, haloalkyl, heteroaryl, or heterocyclyl. The term "phosphinato" refers to —PR$^p$(O)(OR$^p$), where each R$^p$ is independently selected from hydrogen, alkyl, alkenyl, alkynyl, aryl, arylalkyl, cycloalkyl, haloalkyl, heteroaryl, and heterocyclyl.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present disclosure encompasses various stereo isomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise.

Individual stereoisomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereoisomerically-pure intermediates, reagents, and catalysts by well-known asymmetric synthetic methods.

The present disclosure also encompasses isotopically labeled compounds of the present disclosure which are identical to those recited herein, except that one or more atoms are replaced by an atom having an atomic mass or mass number different from the atomic mass or mass number usually found in nature. Examples of isotopes that can be incorporated into compounds of the present disclosure include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the present disclosure can generally be prepared by following procedures analogous to those disclosed herein by substituting an isotopically labeled reagent for a non-isotopically labeled reagent.

The present disclosure also encompasses solvates of compounds described herein. "Solvate" means a physical association of a compound of this present disclosure with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

As used herein, the term "subject" refers to a mammal, including, but not limited to, a human, a non-human primate, and a non-human mammal, such as a bovine, equine, canine, ovine, or feline.

As used herein, the term "patient" refers to a subject that has been diagnosed or otherwise identified as having a condition (e.g., a medical condition) for which a treatment is desired, indicated, or administered.

As used herein, the term "therapeutically effective amount" refers to the amount of a compound (e.g., a compound of the present disclosure) sufficient to effect a medically beneficial result including, for example, by mitigating or eliminating at least one symptom of the condition being treated, or curing (temporarily or permanently) at least one physiological defect that causes or contributes to the disease or condition being treated. A therapeutically effective amount accounts for treatment variables including, for example, dose, duration, timing, and route of administration.

As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical formulation" refers to the combination of at least one active agent and at least one carrier or excipient in a form suitable for administration to a subject.

As used herein, the term "pharmaceutically acceptable salt" refers to any pharmaceutically acceptable salt (e.g., acid or base) of a compound of the present disclosure which, upon administration to a subject, is capable of providing a compound of this disclosure or an active metabolite or residue thereof. As is known to those of skill in the art, "salts" of the compounds of the present disclosure may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the present disclosure and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2- naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present disclosure compounded with a suitable cation such as Na+, $NH_3^+$, and $NHW_4^+$ (wherein W is a $C_{1-4}$ alkyl group), and the like.

For therapeutic use, salts of the compounds of the present disclosure are contemplated as being pharmaceutically acceptable. However, salts of acids and bases that are non-pharmaceutically acceptable may also find use, for example, in the preparation or purification of a pharmaceutically acceptable compound.

Throughout the description, where compositions and kits are described as having, including, or comprising specific components, or where processes and methods are described as having, including, or comprising specific steps, it is contemplated that, additionally, there are compositions and kits of the present disclosure that consist essentially of, or consist of, the recited components, and that there are processes and methods according to the present disclosure that consist essentially of, or consist of, the recited processing steps.

As a general matter, compositions specifying a percentage are by weight unless otherwise specified. Further, if a variable is not accompanied by a definition, then the previous definition of the variable controls.

II. Pharmaceutical Formulations, Kits, and Therapy

Representative examples of diseases and conditions treatable using compounds of the present disclosure are as listed herein above, and include, but are not limited to, lysosomal storage disorders including Niemenn-Pick Type C (NPC), and other disorders of cholesterol homeostasis.

Some embodiments provide for methods of treatment for a lysosomal storage disorder by administering a therapeutically effective amount of a compound of Formulas I-IV or a pharmaceutically acceptable salt thereof. Lysosomal storage disorders include, for example, Niemann-Pick Types A, B, & C, Batten disease, Wolman disease, Griscelli Type 1, Griscelli Type 2, Griscelli Type 3, Salla disease, cystinosis, Fabry disease, Gaucher Type 1, Gaucher Type 2, Sandhoff disease, alpha-mannosidosis, beta-mannosidosis, Ceroid lipofuscinosis, Aspartylglucosaminuria, mucopolysaccharidosis (MPS) Type 1, MPS Type 2, MPS Type 3A, MPS Type 3B, MPS Type 3C, MPS Type 3D, MPS Type IVB, MPS Type VI, MPC Type VII, Schindler disease, Metachromatic leukodystrophy 1, Metachromatic leukodystrophy 2, Tay-Sachs, Sialidosis, Morquio A, Fucosidosis, Pompe disease, Chediak-Higashi, Mucolipidosis 4, GM2 gangliosidosis, Pycnodystostosis, Globoid cell leukodystrophy, Pseudo-Hurler polydystrophy, Ceroid lipofuscinosis 2, Ceroid lipofuscinosis 6, and Ceroid lipofuscinosis 8.

Some embodiments provide for methods of treatment for dyslipidemias by administering a therapeutically effective amount of a compound of Formulas I-IV or a pharmaceutically acceptable salt thereof. Dyslipidemias include, for example, Familial hypercholesterolemia, Lysosomal acid lipase deficiency, Lathosterolosis, Desmosterolosis, CHILD syndrome, Smith-Lemli-Optiz Syndrome, and Tangier disease. Optionally, the method further includes administering a therapeutically effective amount of cyclodextrin to the patient.

Suitable pharmaceutical compositions may be formulated by means known in the art and their mode of administration and dose determined by the skilled practitioner. A compound may be administered by oral or non-oral, e.g., intramuscular, intraperitoneal, intravenous, intracisternal injection or infusion, subcutaneous injection, transdermal or transmucosal routes. Methods well known in the art for making pharmaceutical formulations are found, for example, in "Remington: The Science and Practice of Pharmacy" (20th ed., ed. A. R. Gennaro, 2000, Lippincott Williams & Wilkins).

The compound may be optionally administered as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include calcium, zinc, iron, and the like.

For parenteral administration, a compound may be dissolved in sterile water or saline or a pharmaceutically acceptable vehicle used for administration of non-water soluble compounds such as those used for vitamin K. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes.

In some embodiments, a compound or pharmaceutical formulation in accordance may be administered by means of a medical device or appliance such as an implant, graft, prosthesis, stent, etc. Implants may be devised which are intended to contain and release such compounds or compositions. An example would be an implant made of a polymeric material adapted to release the compound over a period of time (e.g., an osmotic pump).

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc). Formulations for oral use may also be provided as chewable tablets, or as hard gelatin capsules wherein the active ingredient is mixed with an inert solid diluent, or as soft gelatin capsules wherein the active ingredient is mixed with water or an oil medium. Formulations for oral use also include rapidly disintegrating or dissolving dosage forms, also known as fast dissolve, fast or rapid melt, and quick disintegrating dosage forms. These dosage forms dissolve or disintegrate rapidly in the patient's mouth without chewing or the need for water within a short time frame. Because of their ease of administration, such compositions are particularly useful for the specific needs of pediatrics, geriatrics, and patients with dysphagia.

Provided herein are also kits that include a compound of the disclosure, or a pharmaceutically acceptable salt thereof, and suitable packaging. In some embodiments, a kit further includes instructions for use. In some embodiments, a kit includes a compound of the disclosure, or a pharmaceutically acceptable salt thereof, and a label and/or instructions for use of the compounds in the treatment of the indications, including the diseases or conditions, described herein.

Provided herein are also articles of manufacture that include a compound described herein or a pharmaceutically acceptable salt thereof in a suitable container. The container may be a vial, jar, ampoule, preloaded syringe, and intravenous bag.

Administration of compounds in controlled release formulations is useful where the compound of the present disclosure has (i) a narrow therapeutic index (e.g., the difference between the plasma concentration leading to harmful side effects or toxic reactions and the plasma concentration leading to a therapeutic effect is small; generally, the therapeutic index, TI is defined as the ratio of median lethal dose (LD50) or median toxic dose (TD50) to median effective dose (ED50); (ii) a narrow absorption window in the gastro-intestinal tract; or (iii) a short biological half-life, so that frequent dosing during a day is required in order to sustain the plasma level at a therapeutic level.

Many strategies can be pursued to obtain controlled release in which the rate of release outweighs the rate of metabolism of the therapeutic compound. For example, controlled release can be obtained by the appropriate selection of formulation parameters and ingredients, including, e.g., appropriate controlled release compositions and coatings. Examples include single or multiple unit tablet or capsule compositions, oil solutions, suspensions, emulsions, microcapsules, microspheres, nanoparticulate formulations, patches, and liposomes.

The concentration of the compound in the formulation will vary depending upon a number of factors, including the dosage of the drug to be administered, and the route of administration. Ultimately, the concentration of the compound in the formulation is selected such that it can be administered to patients in therapeutically effective amounts. For an amount is administered which prevents, reduces, or eliminates the symptoms of the disease or condition being treated. Typical dose ranges are from about 0.001 mg/kg to about 2 mg/kg of body-weight per day. Desirably, a dose of between 0.001 mg/kg and 1 mg/kg of body weight, or 0.005 mg/kg and 0.5 mg/kg of body weight, is administered. The exemplary dosage of drug to be administered is likely to depend on such variables as the type and extent of the condition, the overall health status of the particular patient, the formulation of the compound, and its route of administration. Standard clinical trials may be used to optimize the dose and dosing frequency for any particular compound.

The compounds of the present disclosure may be administered individually, in combination with each other, and/or in combination with other pharmaceuticals useful for treating the disease or condition of interest. It is understood that the component medications of a combination therapy may be administered to the patient simultaneously or at different times, and may be administered on the same or different dosing schedules, as appropriate. The dosage of each component medication need not be the same and are expected to be different in most cases. Furthermore, the routes of administration may be the same or different. For example, one compound may be administered once daily by intravenous, intramuscular, or subcutaneous injection and another compound may be administered parenterally twice daily. In one embodiment, the component medications are coformulated for convenience (e.g., in the same injectable or ingestible composition).

In one embodiment, combination therapy includes cyclodextrin as described in WO 2014/022841, which is hereby incorporated by reference in its entirety.

III. Fused Heterocyclic Compounds

One aspect of the present disclosure provides heterotricyclic organic compounds such as those in Formula I. These heterotricyclic compounds are contemplated to be useful in the methods, compositions, and kits described herein. Some embodiments provide for a compound of Formula I:

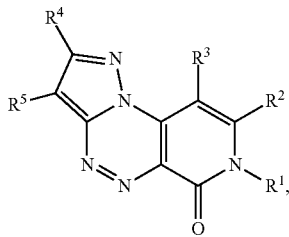

or a pharmaceutically acceptable salt thereof, wherein:

$R^1$ is —$(C_2$-$C_6$ alkylidene)-$NR^6R^7$, —$(C_2$-$C_6$ alkylidene)-$X^1$—$(C_2$-$C_6$ alkylidene)-$NR^6R^7$, or —$(C_3$-$C_6$ cycloalkylidene)-$NR^6R^7$, and is optionally substituted with one or more groups independently selected from $C_1$-$C_6$ alkyl, $C_3$-$C_6$ cycloalkyl, halogen, —OH, alkoxy, —$NO_2$, amino, —CN, —COOH, —$COOR^8$, and amido;

$R^2$, $R^3$, $R^4$, and $R^5$ are independently selected from H, halogen, —CN, amino, —$NO_2$, $C_1$-$C_6$ alkyl, $C_3$-$C_6$ cycloalkyl, alkoxy, —$(C_1$-$C_6$ alkylidene)-$X^2$—$(C_1$-$C_6$ alkyl), aryl, heterocyclyl, heteroaryl, aralkyl, heteroarylalkyl and heterocyclylalkyl, and are optionally substituted with one or more groups independently selected from $C_1$-$C_6$ alkyl, $C_3$-$C_6$ cycloalkyl, halogen, —OH, alkoxy, —$NO_2$, amino, —CN, —COOH, —$COOR^9$, and -amido;

$X^1$ and $X^2$ are independently selected from null, —O—, —S—, —$SO_2$—, —(C═O)—, —$N(R^{11})$—, and —C(O)N($R^{12}$)—, and are optionally substituted with one or more groups independently selected from halogen, —OH, amino, alkoxy, —CN, and —$NO_2$;

$R^6$ and $R^7$ are independently selected from H, $C_1$-$C_6$ alkyl, and $C_3$-$C_6$ cycloalkyl; or $R^6$, $R^7$ and the nitrogen to which they are attached join together to form a heterocyclic ring; and $R^8$, $R^9$, $R^{11}$, and $R^{12}$ are independently selected from H, $C_1$-$C_6$ alkyl, and $C_3$-$C_6$ cycloalkyl.

In some embodiments, $R^1$ is —$(C_2$-$C_6$ alkylidene)-$NR^6R^7$, —$(C_2$-$C_6$ alkylidene)-$X^1$—$(C_2$-$C_6$ alkylidene)-$NR^6R^7$, or —$(C_3$-$C_6$ cycloalkylidene)-$NR^6R^7$.

In certain embodiments, $R^1$ is —$(C_2$-$C_8$ alkylidene)-$NR^6R^7$. In certain embodiments, $R^1$ is —$(C_2$-$C_6$ alkylidene)-$NR^6R^7$.

In certain embodiments, $R^6$ and $R^7$ are independently selected from H or $C_1$-$C_6$ alkyl. In certain embodiments, $R^6$ and $R^7$ are each $C_1$-$C_6$ alkyl. In certain other embodiments, $R^6$ and $R^7$ and the nitrogen to which they are attached form a ring. In certain other embodiments, $R^6$ and $R^7$ and the nitrogen to which they are attached form a morpholine, piperidine, or pyrrolidine ring.

In some embodiments, $R^2$, $R^3$, $R^4$, and $R^5$ are independently selected from H, halogen, —CN, amino, —$NO_2$, $C_1$-$C_6$ alkyl, $C_3$-$C_6$ cycloalkyl, alkoxy, —$(C_1$-$C_6$ alkylidene)-$X^2$—$(C_1$-$C_6$ alkyl), aryl, heterocyclyl, heteroaryl, aralkyl, heteroarylalkyl and heterocyclylalkyl.

In some embodiments, $R^2$, $R^3$, and $R^4$ are independently selected from H, halogen, $C_1$-$C_6$ alkyl, alkoxy, —$(C_1$-$C_6$ alkylidene)-$X^2$—$(C_1$-$C_6$ alkyl), $C_3$-$C_6$ cycloalkyl, aryl, heterocyclyl, and heteroaryl. In some embodiments, $R^2$ is H. In some embodiments, $R^3$ is H.

In some embodiments, $R^4$ is H. In some embodiments, $R^4$ is $C_1$-$C_6$ alkyl. In some embodiments, $R^4$ is alkoxy. In some embodiments, $R^4$ is —$(C_1$ to $C_6$ alkylidene)-$X^2$—$(C_1$ to $C_6$ alkyl), In certain embodiments, $R^5$ is an aryl or heteroaryl, wherein the aryl or heteroaryl optionally substituted with one or more groups independently selected from $C_1$-$C_6$ alkyl, $C_3$-$C_6$ cycloalkyl, halogen, —OH, alkoxy, —$NO_2$, amino, —CN, —COOH, —$COOR^9$, and amido. In certain embodiments, $R^5$ is an aryl or heteroaryl, wherein the aryl or heteroaryl optionally substituted with one or more halo. In certain embodiments, $R^5$ is an aryl or heteroaryl group. In certain embodiments, $R^5$ is an aryl or heteroaryl group and $R^4$ is H, $C_1$ to $C_6$ alkyl, or —$CH_2OCH_3$.

In certain embodiments, the compound is one of those listed in Table 1 below.

TABLE 1

| | | |
|---|---|---|
| 1 | 11-[3-(Dimethylamino)propyl]-5-(p-fluorophenyl)-2.3.7.8.11-pentazatricyclo[7.4.0.0²,⁶]trideca-1(9),3,5,7,12-pentaen-10-one | 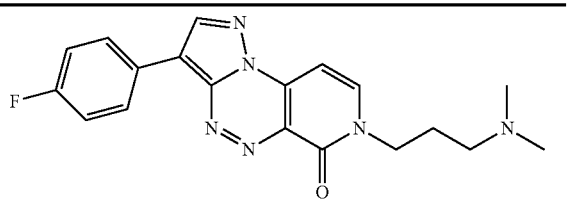 |
| 2 | 11-[3-(Dimethylamino)propyl]-5-(p-fluorophenyl)-4-methyl-2.3.7.8.11-pentazatricyclo[7.4.0.0²,⁶]trideca-1(9),3,5,7,12-pentaen-10-one | 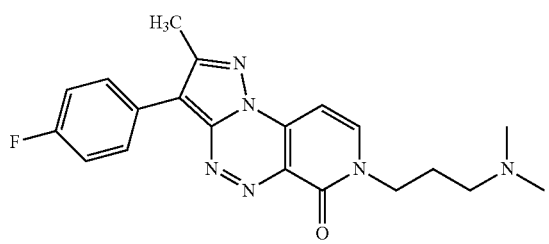 [SMILES: Cc1nn2c(nnc3c(=O)n(CCCN(C)C)ccc32)c1-c1ccc(F)cc1] |

TABLE 1-continued

| | | |
|---|---|---|
| 3 | 11-[3-(Dimethylamino)propyl]-5-phenyl-2.3.7.8.11-pentazatricyclo[7.4.0.0²,⁶]trideca-1(9),3,5,7,12-pentaen-10-one | 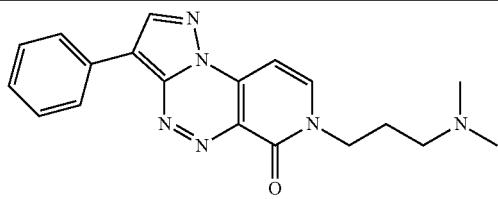 |
| 4 | 11-[3-(Dimethylamino)propyl]-4-ethyl-5-(p-fluorophenyl)-2.3.7.8.11-pentazatricyclo[7.4.0.0²,⁶]trideca-1(9),3,5,7,12-pentaen-10-one | 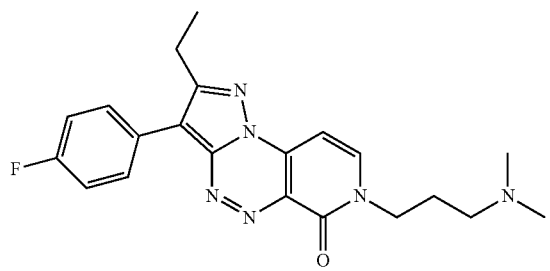 [SMILES: CCc1nn2c(nnc3c(=O)n(CCCN(C)C)ccc32)c1-c1ccc(F)cc1] |
| 5 | 11-[2-(Dimethylamino)ethyl]-4-ethyl-5-phenyl-2.3.7.8.11-pentazatricyclo[7.4.0.0²,⁶]trideca-1(9),3,5,7,12-pentaen-10-one | 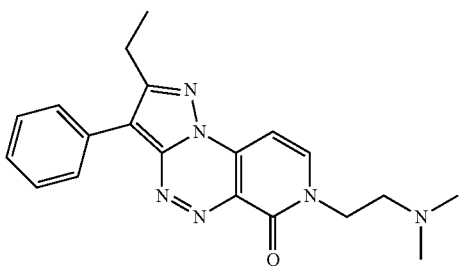 [SMILES: CCc1nn2c(nnc3c(=O)n(CCN(C)C)ccc32)c1-c1ccccc1] |
| 6 | 11-[2-(Dimethylamino)ethyl]-5-(p-fluorophenyl)-2.3.7.8.11-pentazatricyclo[7.4.0.0²,⁶]trideca-1(9),3,5,7,12-pentaen-10-one | 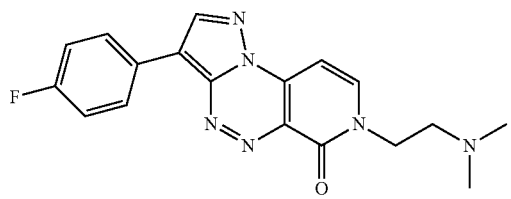 [SMILES: CN(C)CCn1ccc2c(nnc3c(-c4ccc(F)cc4)cnn32)c1=O] |
| 7 | 5-(p-Fluorophenyl)-4-methyl-11-(3-morpholinopropyl)-2.3.7.8.11-pentazatricyclo[7.4.0.0²,⁶]trideca-1(9),3,5,7,12-pentaen-10-one | 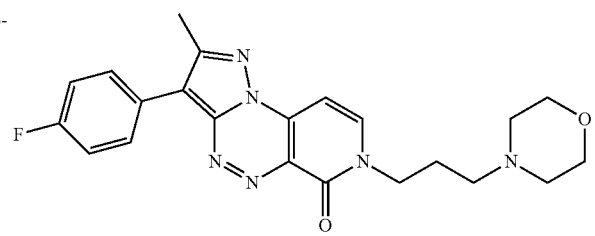 |
| 8 | 5-(p-Chlorophenyl)-11-[3-(dimethylamino)propyl-2.3.7.8.11-pentazatricyclo[7.4.0.0²,⁶]trideca-1(9),3,5,7,12-pentaen-10-one | 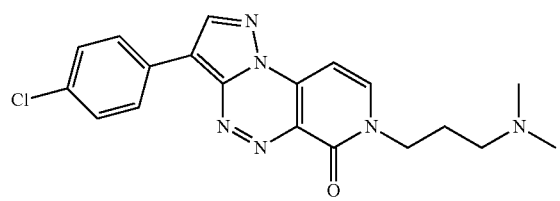 [SMILES: CN(C)CCCn1ccc2c(nnc3c(-c4ccc(Cl)cc4)cnn32)c1=O] |

Another aspect of the present disclosure provides heterotricyclic organic compounds such as those in Formula II. These heterotricyclic compounds are contemplated to be useful in the methods, compositions, and kits described herein. Some embodiments provide for a compound of Formula II:

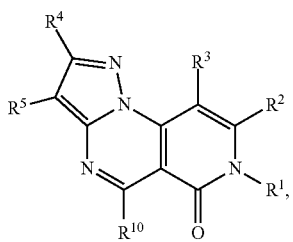

II or a pharmaceutically acceptable salt thereof, wherein:

$R^1$ is —($C_2$-$C_6$ alkylidene)-$NR^6R^7$, —($C_2$-$C_6$ alkylidene)-$X^1$—($C_2$-$C_6$ alkylidene)-$NR^6R^7$, or —($C_3$-$C_6$ cycloalkylidene)-$NR^6R^7$, and is optionally substituted with one or more groups independently selected from $C_1$-$C_6$ alkyl, $C_3$-$C_6$ cycloalkyl, halogen, —OH, alkoxy, —$NO_2$, amino, —CN, —COOH, —$COOR^8$, and amido;

$R^2$, $R^3$, $R^4$, and $R^5$ are independently selected from H, halogen, —CN, amino, —$NO_2$, $C_1$-$C_6$ alkyl, $C_3$-$C_6$ cycloalkyl, alkoxy, —($C_1$-$C_6$ alkylidene)-$X^2$—($C_1$-$C_6$ alkyl), aryl, heterocyclyl, heteroaryl, aralkyl, heteroarylalkyl, and heterocyclylalkyl, and are optionally substituted with one or more groups independently selected from $C_1$-$C_6$ alkyl, $C_3$-$C_6$ cycloalkyl, halogen, —OH, alkoxy, —$NO_2$, amino, —CN, —COOH, —$COOR^9$, and amido;

$X^1$ and $X^2$ are independently selected from null, —O—, —S—, —$SO_2$—, —(C=O)—, —N($R^{11}$)—, and —C(O)N($R^{12}$)—, and are optionally substituted with one or more groups independently selected from halogen, —OH, amino, alkoxy, —CN, and —$NO_2$;

$R^6$ and $R^7$ are independently selected from H, $C_1$-$C_6$ alkyl, and $C_3$-$C_6$ cycloalkyl; or $R^6$, $R^7$ and the nitrogen to which they are attached join together to form a heterocyclic ring;

$R^8$, $R^9$, $R^{11}$, and $R^{12}$ are independently selected from H, $C_1$-$C_6$ alkyl, and $C_3$-$C_6$ cycloalkyl; and $R^{10}$ is H, $C_1$-$C_6$ alkyl, $C_3$-$C_6$ cycloalkyl, or halogen.

In some embodiments, $R^1$ is —($C_2$-$C_6$ alkylidene)-$NR^6R^7$, —($C_2$-$C_6$ alkylidene)-$X^1$—($C_2$-$C_6$ alkylidene)-$NR^6R^7$, or —($C_3$-$C_6$ cycloalkylidene)-$NR^6R^7$.

In certain embodiments, $R^1$ is —($C_2$-$C_8$ alkylidene)-$NR^6R^7$. In certain embodiments, $R^1$ is —($C_2$-$C_6$ alkylidene)-$NR^6R^7$.

In certain embodiments, $R^6$ and $R^7$ are independently selected from H or $C_1$-$C_6$ alkyl. In certain embodiments, $R^6$ and $R^7$ are each $C_1$-$C_6$ alkyl. In certain other embodiments, $R^6$ and $R^7$ and the nitrogen to which they are attached form a ring. In certain other embodiments, $R^6$ and $R^7$ and the nitrogen to which they are attached form a morpholine, piperidine, or pyrrolidine ring.

In some embodiments, $R^2$, $R^3$, $R^4$, and $R^5$ are independently selected from H, halogen, —CN, amino, —$NO_2$, $C_1$-$C_6$ alkyl), $C_3$-$C_6$ cycloalkyl, alkoxy, —($C_1$-$C_6$ alkylidene)-$X^2$-($C_1$-$C_6$ alkyl), aryl, heterocyclyl, heteroaryl, aralkyl, heteroarylalkyl and heterocyclylalkyl.

In some embodiments, $R^2$, $R^3$, and $R^4$ are independently selected from H,-halogen, $C_1$-$C_6$ alkyl, alkoxy, —($C_1$-$C_6$ alkylidene)-$X^2$—($C_1$-$C_6$ alkyl), $C_3$-$C_6$ cycloalkyl, aryl, heterocyclyl, and heteroaryl. In some embodiments, $R^2$ is H. In some embodiments, $R^3$ is H.

In some embodiments, $R^4$ is H. In some embodiments, $R^4$ is $C_1$-$C_6$ alkyl. In some embodiments, $R^4$ is alkoxy. In some embodiments, $R^4$ is —($C_1$-$C_6$ alkylidene)-$X^2$—($C_1$-$C_6$ alkyl).

In certain embodiments, $R^5$ is an aryl or heteroaryl, wherein the aryl or heteroaryl optionally substituted with one or more groups independently selected from $C_1$-$C_6$ alkyl, $C_3$-$C_6$ cycloalkyl, halogen, —OH, alkoxy, —$NO_2$,- amino, —CN, —COOH, —$COOR^9$, and amido. In certain embodiments, $R^5$ is an aryl or heteroaryl, wherein the aryl or heteroaryl optionally substituted with one or more halo.

In certain embodiments, $R^5$ is an aryl or heteroaryl group. In certain embodiments, $R^5$ is an aryl or heteroaryl group and $R^4$ is H, $C_1$-$C_6$ alkyl), or —$CH_2OCH_3$.

In certain embodiments, $R^{10}$ is $C_1$-$C_6$ alkyl or halogen. In some embodiments, $R^{10}$ is H.

In certain embodiments, the compound is one of those in the Table 2 below.

TABLE 2

| 9 | 11-[3-(Dimethylamino)propyl]-5-phenyl-2.3.7.11-tetrazatricyclo[7.4.0.0²,⁶]trideca-1(9),3,5,7,12-pentaen-10-one | 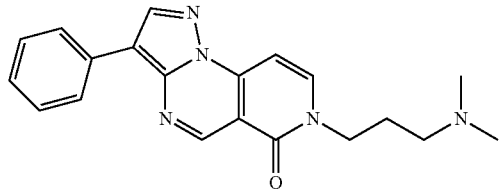 [SMILES: CN(C)CCCn1ccc2c(cnc3c(-c4ccccc4)cnn32)c1=O] |
| --- | --- | --- |
| 10 | 11-[3-(Dimethylamino)propyl]-4-(methoxymethyl)-5-phenyl-2.3.7.11-tetrazatricyclo[7.4.0.0²,⁶]trideca-1(9),3,5,7,12-pentaen-10-one | 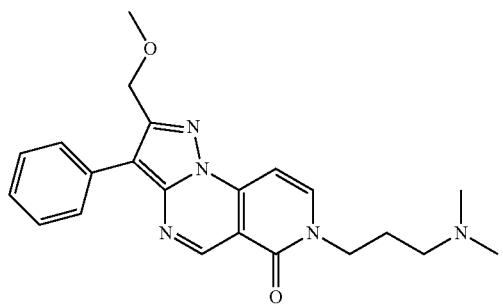 [SMILES: COCc1nn2c(ncc3c(=O)n(CCCN(C)C)ccc32)c1-c1ccccc1] |

TABLE 2-continued

| 11 | 5-(p-Chlorophenyl)-11-[3-(dimethylamino)propyl]-2.3.7.11-tetrazatricyclo[7.4.0.0^{2,6}]trideca-1(9),3,5,7,12-pentaen-10-one |  |

Another aspect of the present disclosure provides heterotricyclic organic compounds such as those in Formula III. These heterotricyclic compounds are contemplated to be useful in the methods, compositions, and kits described herein. Some embodiments provide for a compound of Formula III:

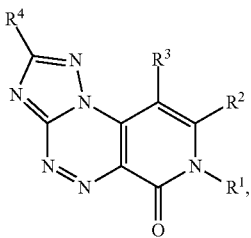

III or a pharmaceutically acceptable salt thereof, wherein:

$R^1$ is —($C_2$-$C_6$ alkylidene)-$NR^6R^7$, —($C_2$-$C_6$ alkylidene)-$X^1$—($C_2$-$C_6$ alkylidene)-$NR^6R^7$, or —($C_3$-$C_6$ cycloalkylidene)-$NR^6R^7$, and is optionally substituted with one or more groups independently selected from $C_1$-$C_6$ alkyl, $C_3$-$C_6$ cycloalkyl, halogen, —OH, alkoxy, —$NO_2$, -amino, —CN, —COOH, —$COOR^8$, and amido;

$R^2$, $R^3$ and $R^4$ are independently selected from H, halogen, —CN, amino, —$NO_2$, $C_1$-$C_6$ alkyl, $C_3$-$C_6$ cycloalkyl, alkoxy, —($C_1$-$C_6$ alkylidene)-$X^2$—($C_1$-$C_6$ alkyl), aryl, heterocyclyl, heteroaryl, aralkyl, heteroarylakyl and heterocyclylalkyl, and are optionally substituted with one or more groups independently selected from $C_1$-$C_6$ alkyl, $C_3$-$C_6$ cycloalkyl, halogen, —OH, alkoxy, —$NO_2$, amino, —CN, —COOH, —$COOR^9$, and amido;

$X^1$ and $X^2$ are independently selected from null, —O—, —S—, —$SO_2$—, —(C=O)—, —N($R^{11}$)—, and —C(O)N($R^{12}$)—, and are optionally substituted with one or more groups independently selected from halogen, —OH, amino, alkoxy, —CN, and —$NO_2$;

$R^6$ and $R^7$ are independently selected from H, $C_1$-$C_6$ alkyl, and $C_3$-$C_6$ cycloalkyl; or $R^6$, $R^7$ and the nitrogen to which they are attached join together to form a heterocyclic ring; and $R^8$, $R^9$, $R^{11}$, and $R^{12}$ are independently selected from H, $C_1$-$C_6$ alkyl, and $C_3$-$C_6$ cycloalkyl.

In certain embodiments, $R^1$ is —($C_2$-$C_8$ alkylidene)-$NR^6R^7$. In certain embodiments, $R^1$ is —($C_2$-$C_6$ alkylidene)-$NR^6R^7$.

In certain embodiments, $R^6$ and $R^7$ are each $C_1$-$C_6$ alkyl. In certain other embodiments, $R^6$ and $R^7$ and the nitrogen to which they are attached form a ring. In certain other embodiments, $R^6$ and $R^7$ and the nitrogen to which they are attached form a morpholine, piperidine, or pyrrolidine ring.

In some embodiments, $R^2$, $R^3$, and $R^4$ are independently selected from H, halogen, —CN, amino, —$NO_2$, $C_1$-$C_6$ alkyl, $C_3$-$C_6$ cycloalkyl, alkoxy, —($C_1$-$C_6$ alkylidene)-$X^2$—($C_1$-$C_6$ alkyl), aryl, heterocyclyl, heteroaryl, aralkyl, heteroarylalkyl and heterocyclylalkyl.

In some embodiments, $R^2$, $R^3$, and $R^4$ are independently selected from H, halogen, $C_1$-$C_6$ alkyl, alkoxy, —($C_1$-$C_6$ alkylidene)-$X^2$—($C_1$-$C_6$ alkyl), $C_3$-$C_6$ cycloalkyl), aryl, heterocyclyl, and heteroaryl. In some embodiments, $R^2$ is H. In some embodiments, $R^3$ is H.

In some embodiments, $R^4$ is H. In some embodiments, $R^4$ is $C_1$-$C_6$ alkyl. In some embodiments, $R^4$ is alkoxy. In some embodiments, $R^4$ is —($C_1$-$C_6$ alkylidene)-$X^2$—($C_1$-$C_6$ alkyl).

In certain embodiments, $R^4$ is an aryl or heteroaryl, each of which are optionally substituted with one or more groups independently selected from $C_1$-$C_6$ alkyl, $C_3$-$C_6$ cycloalkyl, halogen, —OH, alkoxy, —$NO_2$, amino, —CN, —COOH, —$COOR^9$, and amido.

In certain embodiments, $R^4$ is an aryl or heteroaryl group.

Another aspect of the present disclosure provides heterotricyclic organic compounds such as those in Formula IV. These heterotricyclic compounds are contemplated to be useful in the methods, compositions, and kits described herein. Some embodiments provide for a compound of Formula IV:

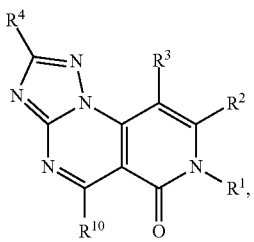

IV or a pharmaceutically acceptable salt thereof, wherein:

$R^1$ is —($C_2$-$C_6$ alkylidene)-$NR^6R^7$, —($C_2$-$C_6$ alkylidene)-$X^1$—($C_2$-$C_6$ alkylidene)-$NR^6R^7$, or —($C_3$-$C_6$ cycloalkylidene)—$NR^6R^7$, and is optionally substituted with one or more groups independently selected from $C_1$-$C_6$ alkyl), $C_3$-$C_6$ cycloalkyl), halogen, —OH, alkoxy, —$NO_2$, amino, —CN, —COOH, —$COOR^8$, and amido;

$R^2$, $R^3$, and $R^4$ are independently selected from H, halogen, —CN, amino, —$NO_2$, $C_1$-$C_6$ alkyl, $C_3$-$C_6$ cycloalkyl, alkoxy, —($C_1$-$C_6$ alkylidene)-$X^2$—($C_1$-$C_6$ alkyl), aryl, heterocyclyl, heteroaryl, aralkyl, and heterocyclylalkyl, and are optionally substituted with one or more groups independently selected from $C_1$-$C_6$ alkyl, $C_3$-$C_6$ cycloalkyl, halogen, —OH, alkoxy, —$NO_2$, amino, —CN, —COOH, —$COOR^S$, and amido;

$X^1$ and $X^2$ are independently selected from null, —O—, —S—, —$SO_2$—, —(C=O)—, —N($R^{11}$)—, and —C(O)N ($R^{12}$)—, and are optionally substituted with one or more groups independently selected from halogen, —OH, amino, alkoxy, —CN, and —NO$_2$;

$R^6$ and $R^7$ are independently selected from H, $C_1$-$C_6$ alkyl), and $C_3$-$C_6$ cycloalkyl; or $R^6$, $R^7$ and the nitrogen to which they are attached join together to form a heterocyclic ring; and $R^8$, $R^9$, $R^{11}$ and $R^{12}$ are independently selected from H, $C_1$-$C_6$ alkyl, and $C_3$-$C_6$ cycloalkyl; and $R^{10}$ is H, $C_1$-$C_6$ alkyl, $C_3$-$C_6$ cycloalkyl, or halogen.

In certain embodiments, $R^1$ is —($C_2$-$C_8$ alkylidene)NR$^6$R$^7$. In certain embodiments, $R^1$ is —($C_2$-$C_6$ alkylidene)NR$^6$R$^7$.

In certain embodiments, $R^7$ and $R^8$ are each $C_1$-$C_6$ alkyl. In certain other embodiments, $R^6$ and $R^7$ and the nitrogen to which they are attached form a ring. In certain other embodiments, $R^6$ and $R^7$ and the nitrogen to which they are attached form a morpholine, piperidine, or pyrrolidine ring.

In certain embodiments, $R^2$, $R^3$, and $R^4$ are independently selected from H, halogen, $C_1$-$C_6$ alkyl, alkoxy, —($C_1$-$C_6$ alkylidene)-$X^2$—($C_1$-$C_6$ alkyl), $C_3$-$C_6$ cycloalkyl), aryl, heterocyclyl, heteroaryl, aralkyl, and heterocyclylalkyl. In some embodiments, $R^2$ is H. In some embodiments, $R^3$ is H.

In certain embodiments, $R^{10}$ is alkyl or halogen. In certain embodiments, $R^{10}$ is $C_1$-$C_6$ alkyl or halogen. In certain embodiments, $R^{10}$ is $C_1$-$C_6$ alkyl. In some embodiments, $R^{10}$ is hydrogen.

In certain embodiments, $R^4$ is an aryl or heteroaryl group. In certain embodiments, $R^4$ is an aryl. In certain embodiments, $R^4$ is hydrogen. In certain embodiments, the compound is one of those in Table 3.

sures, and should not be regarded as in any manner limiting the scope or spirit of the disclosure. Starting materials shown in the schemes can be obtained from commercial sources or can be made using procedures described in the literature.

Synthesis of Compounds of Formula I

Pyrazoles are well-known compounds and procedures for their preparation have been widely described in the literature. General reviews are described in, for example, "Approaches towards the synthesis of 5-aminopyrazoles", Beilstein Journal of Organic Chemistry, 2011, vol 7, 179-197; "Chemistry of 5-aminopyrazoles: Structure, Synthesis and Reactions", Elmaaty, TMA, LAP LAMBERT Academic Publishing (2012); and "Recent developments in aminopyrazole chemistry", Anwar, H F and Elnagdi M H, Arkivoc, 2009, 198-250. An example of one such synthetic approach ("Synthesis and muscle-relaxant properties of 3-amino-4-arylpyrazoles", Anderson, E L and co-authors, Journal of Medicinal Chemistry (1964), 7, 259-268) is shown in Scheme 1.

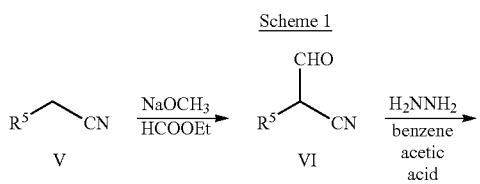

TABLE 3

| 12 | 8-Methyl-11-(3-morpholinopropyl)-2.3.5.7.11-pentazatricyclo[7.4.0.0$^{2,6}$]trideca-1(9),3,5,7,12-pentaen-10-one | 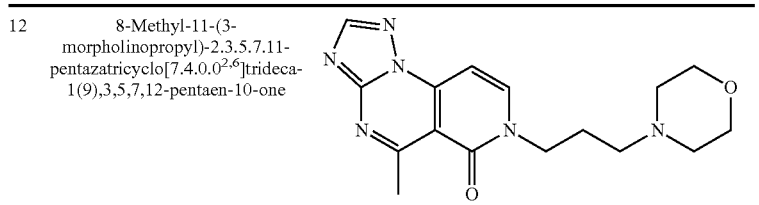 |
| --- | --- | --- |
| 13 | 11-[3-(Dimethylamino)propyl]-4-phenyl-2.3.5.7.11-pentazatricyclo[7.4.0.0$^{2,6}$]trideca-1(9),3,5,7,12-pentaen-10-one | 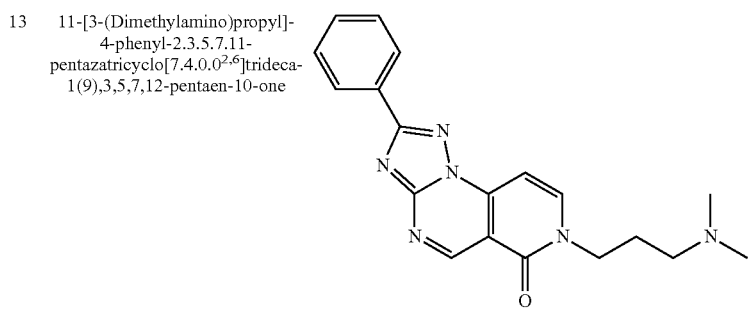 |

The description above describes multiple embodiments relating to compounds of Formulas I, II, III and IV. The patent application specifically contemplates all combinations of the embodiments. For example, the present disclosure contemplates a compound of Formula I in which $R^1$ is —($C_2$-$C_8$ alkylidene)-NR$^6$R$^7$; and $R^4$ is aryl.

In certain embodiments, the compound is one of the following, or pharmaceutically acceptable salt thereof.

IV. Synthesis of Fused Heterocyclic Compounds

Methods for the synthesis of the compounds of this disclosure are shown in the following schemes. These schemes are given for the purpose of illustrating the disclo- -continued VIIa -continued

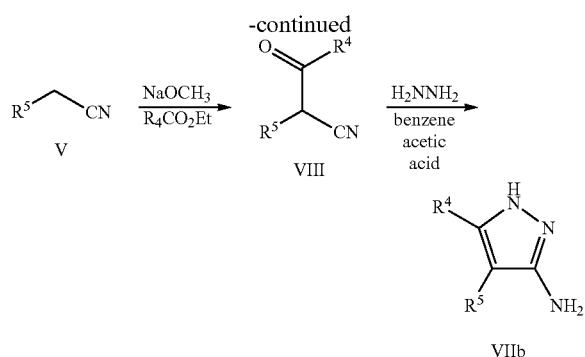

In this Scheme a primary nitrile derivative is treated with sodium methoxide and ethyl formate to give a nitrile aldehyde VI. Treating this intermediate with hydrazine in the presence of acetic acid in benzene gives the 4-substituted 5-aminopyrazole VIIa. Similar methods provide 3,4-disubstituted 5-aminopyrazoles VIIb from nitriles V and suitable esters as shown in Scheme 1. Detailed methods for these transformations may be found in Anderson, E L and co-authors, Journal of Medicinal Chemistry (1964), 7, 259-268, and in US Patent Publication No. 2013/015025, each of which is incorporated into this application its entirety by reference.

In the event that the nitrile V is not commercially available, it may be prepared by any of a number of methods as reviewed in Chapter 3.18, "Nitriles: General Methods and Aliphatic Nitriles" by Michael North in volume 3 of the collection "Comprehensive Organic Functional Group Transformations" $1^{st}$ edition, (Katrinsky, A R; Meth-Cohn O; and Rees C W editors), Elsevier Science (1995), the contents of which are incorporated into this application in their entirety by reference. Representative methods include displacement of an alkyl halide or sulfonate with cyanide ion ("High-yielding, large-scale synthesis of N-protected-β-aminonitriles: tert-butyl (1R)-2-cyano-1-phenylethylcarbamate", Mosa, F; Thirsk C; Vaultier M; Maw G; Whiting A in "Organic Syntheses"(2008), volume 85, 219-230), and amidation of a carboxylic acid with ammonia ("Isobutyramide", Kent, R E; McElvain S M in Organic Syntheses, Volume 3 page 490 (1955) followed by dehydration ("2-Ethylhexanonitrile, Krynitsy, J A; and Carhart H W in Organic Syntheses (1963), collective volume 4, page 436 as shown in Scheme 2.

Scheme 2

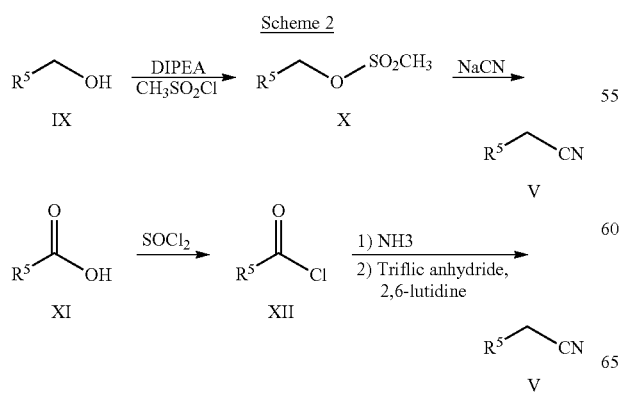

Scheme 3 shows the conversion of an aminopyrazole VII to a final product of type I. Diazotization with sodium nitrite and hydrochloric acid gives the diazonium ion XIII, which undergoes diazo coupling with suitably electron-rich aromatics such as XIV under buffered conditions ("Synthesis of new azocompounds and fused pyrazolo[5,1-c][1,2,2]triazines using heterocyclic components", Ledenyova IV and coauthors, "Journal of Heterocyclic Chemistry", volume 50, 573 (2013), which is incorporated into this application in its entirety by reference). Cyclization under conditions of heating in polyphosphoric acid gives the fused tricyclic compound XVI, which can be alkylated with a suitable bromide, iodide, chloride, or sulfonate ester under basic conditions to give I. In some cases it will be apparent to those of ordinary skill in the art that the use of protecting groups in the alkylating reagent will give superior yields. For example, in the case in which $R^1$=—$CH_2CH_2CH_2NHCH_3$, the alkylation may be performed using Br—$CH_2CH_2CH_2N(CH_3)$ Boc, where Boc represents the tert-butoxycarbamate protecting group. The Boc group would then be cleaved in a separate, post-alkylation step using a suitable reagent such at trifluroacetic acid to generate the final compound. The selection, attachment and removal of protecting groups in organic synthesis is well known to those of ordinary skill in the art, and is summarized in the book "Greene's Protective Groups in Organic Synthesis", $4^{th}$ edition, Wuts, PGM and Greene T W authors, Wiley and Sons, 2006, the content s of which are incorporated into this application in their entirety by reference.

Scheme 3

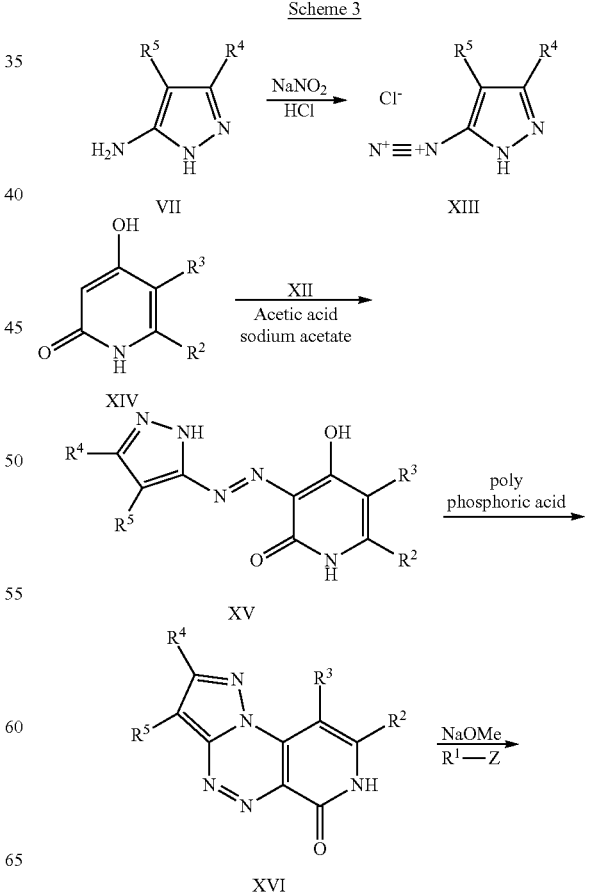

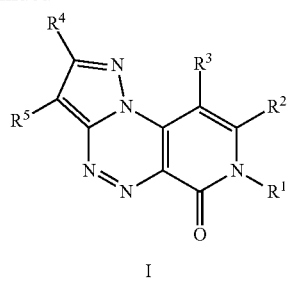

In the event that the required 4-hydroxypyridone XIV is not commercially available, it can be prepared by one of a number of routes. The first of these is illustrated in Scheme 4. Treating carboxylic acids XVII with carbonyldiimidazole gives imidazolides XVIII. Deprotonation of dioxinone XIX with lithium hexamethyldisilazide followed by treatment with XVIII gives the acylated products XX, which are converted to the enamines XXI upon treatment with ammonium acetate in ethanol. Heating XXI in toluene gives the required intermediates XIV ("Synthesis of 6-substituted-4-hydroxy-2-pyridones via intramolecular ketene trapping of functionalized enamine-dioxinones", Patel B H and co-authors, "Organic Letters" (2011), vol. 13, 5156-5159).

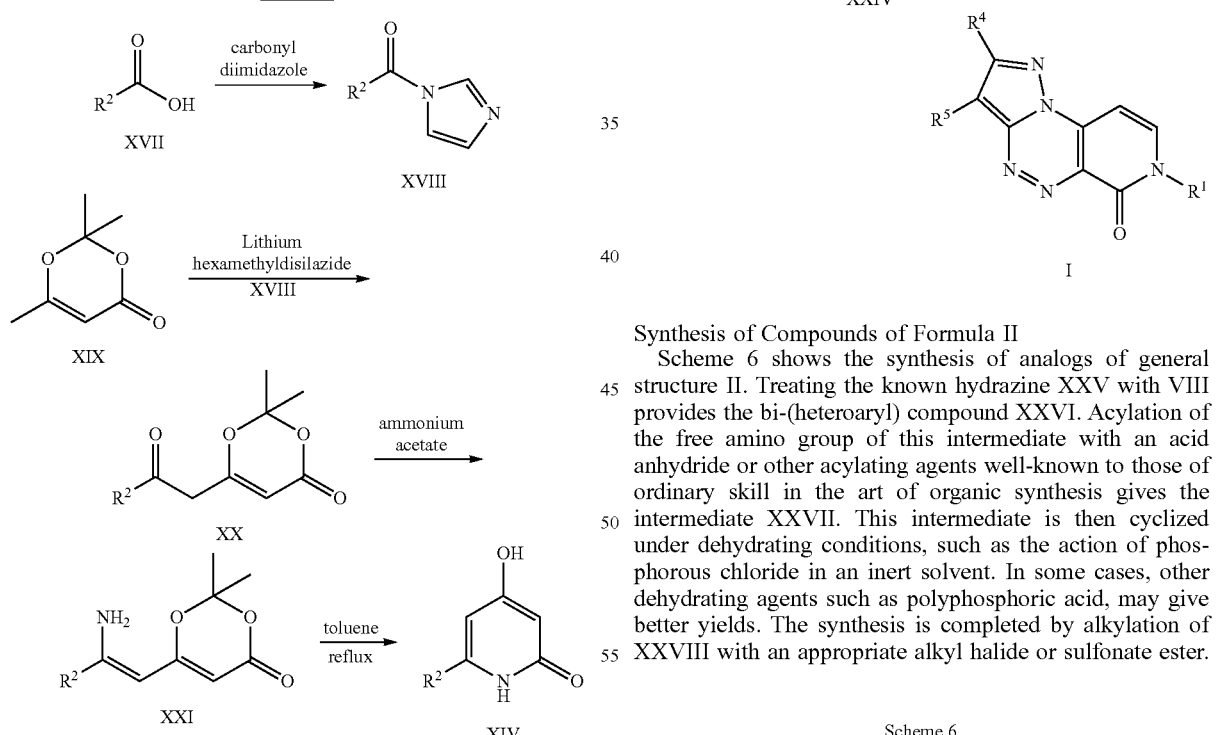

Scheme 5 shows an alternative method for the synthesis of analogs of type I. In this route, the fused ring intermediate XXIII is prepared by treating the diazonium ion XIII with the known enol ether XXII in dimethylformamide as solvent. XXIII is then converted to XXIV by treatment with dimethylformamide dimethylacetal in DMF followed by cyclization with an amine $R^1NH_2$ in acetic acid to give I.

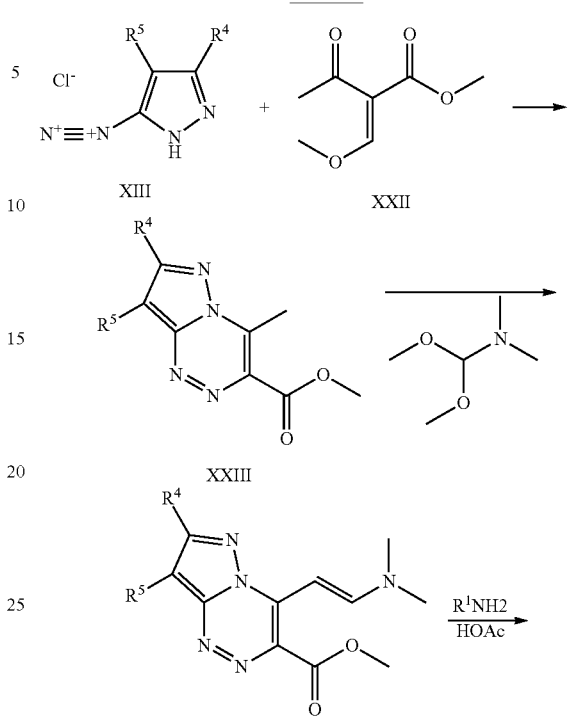

Synthesis of Compounds of Formula II

Scheme 6 shows the synthesis of analogs of general structure II. Treating the known hydrazine XXV with VIII provides the bi-(heteroaryl) compound XXVI. Acylation of the free amino group of this intermediate with an acid anhydride or other acylating agents well-known to those of ordinary skill in the art of organic synthesis gives the intermediate XXVII. This intermediate is then cyclized under dehydrating conditions, such as the action of phosphorous chloride in an inert solvent. In some cases, other dehydrating agents such as polyphosphoric acid, may give better yields. The synthesis is completed by alkylation of XXVIII with an appropriate alkyl halide or sulfonate ester.

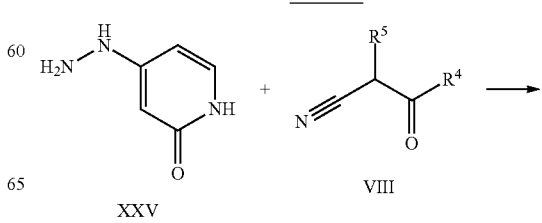

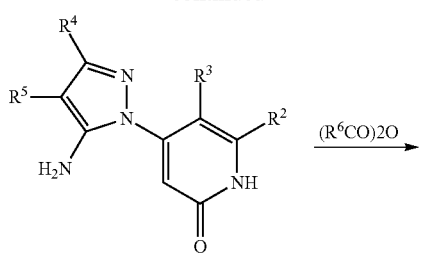

XXVI

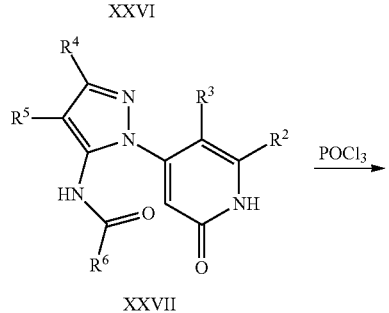

XXVII

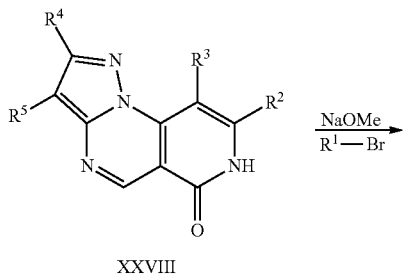

XXVIII

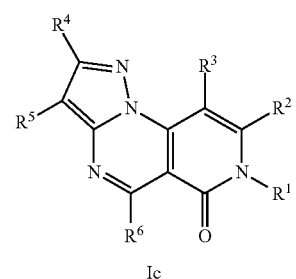

Ic

Scheme 7 shows an alternative method for the preparation of analogs of type II. In this method, an aminopyrazole of type VI is treated with dimethylformamide dimethylacetal in dimethylformamide as solvent gives the enamine XXX. Treating XXX with an amine R₁NH₂ in acetic acid gives II.

Scheme 7

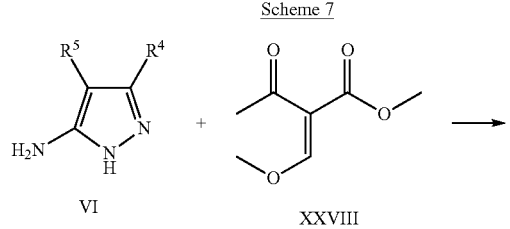

VI          XXVIII

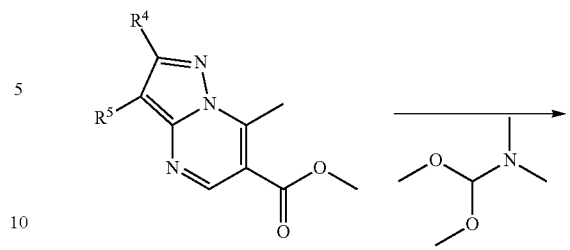

XXIX

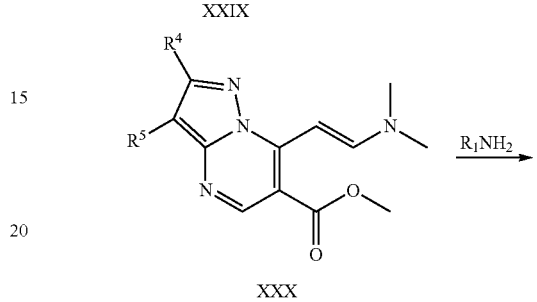

XXX

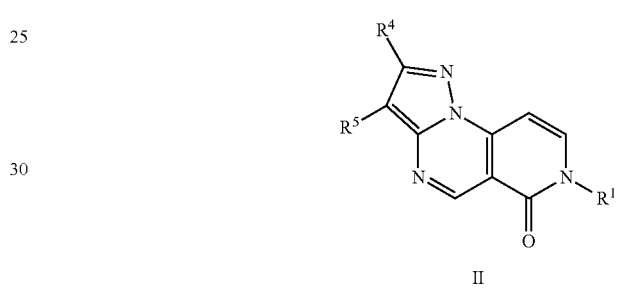

II

Synthesis of Compounds of Formula III

A variety of methods are available for the synthesis of 5-amino-1,2,4-triazoles IX, as summarized in "Amino-1,2,4-triazoles", Chapter 5 of "Triazoles 1,2,4" in the book series "Chemistry of Heterocyclic Compounds: A Series of Monographs", Weissberger A and Taylor E C editors, Wiley and Sons, 1981, the contents of which are incorporated into this application in their entirety by reference. The most important and widely used of these is illustrated in Scheme 8 ("A Convenient Synthesis of Highly Substituted 3-N,N-Dialkylamino-1,2,4-triazoles", Batchelor D V and co-authors, SynLett (2008), 2421-2424; Maffrand J. P and co-authors, "European Journal of Medicinal Chemistry, 1978, 469). A carboxylic ester XXXI is treated with hydrazine to produce the corresponding hydrazide XXXII. Treating this hydrazide with commercially available methyl isothiouronium sulfate XXXV and heating gives the aminotriazole XXXIV.

Scheme 8

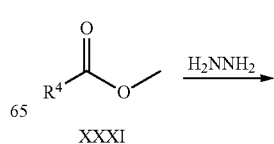

XXXI

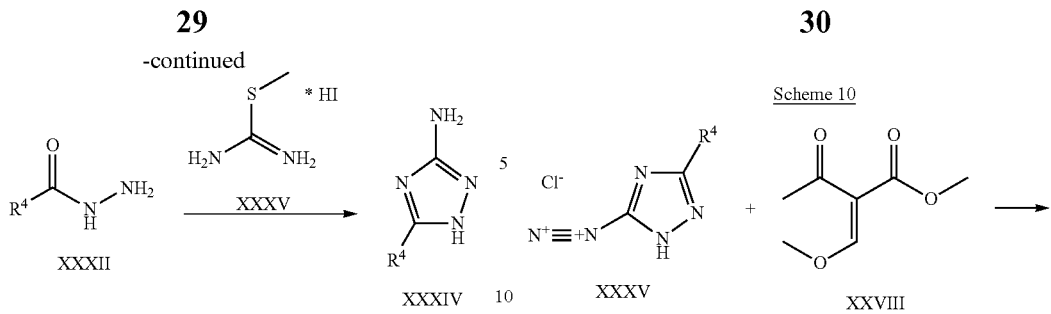

Subjecting these triazoles to a synthetic route similar to that in Scheme 3 gives the analogs III (Scheme 9).

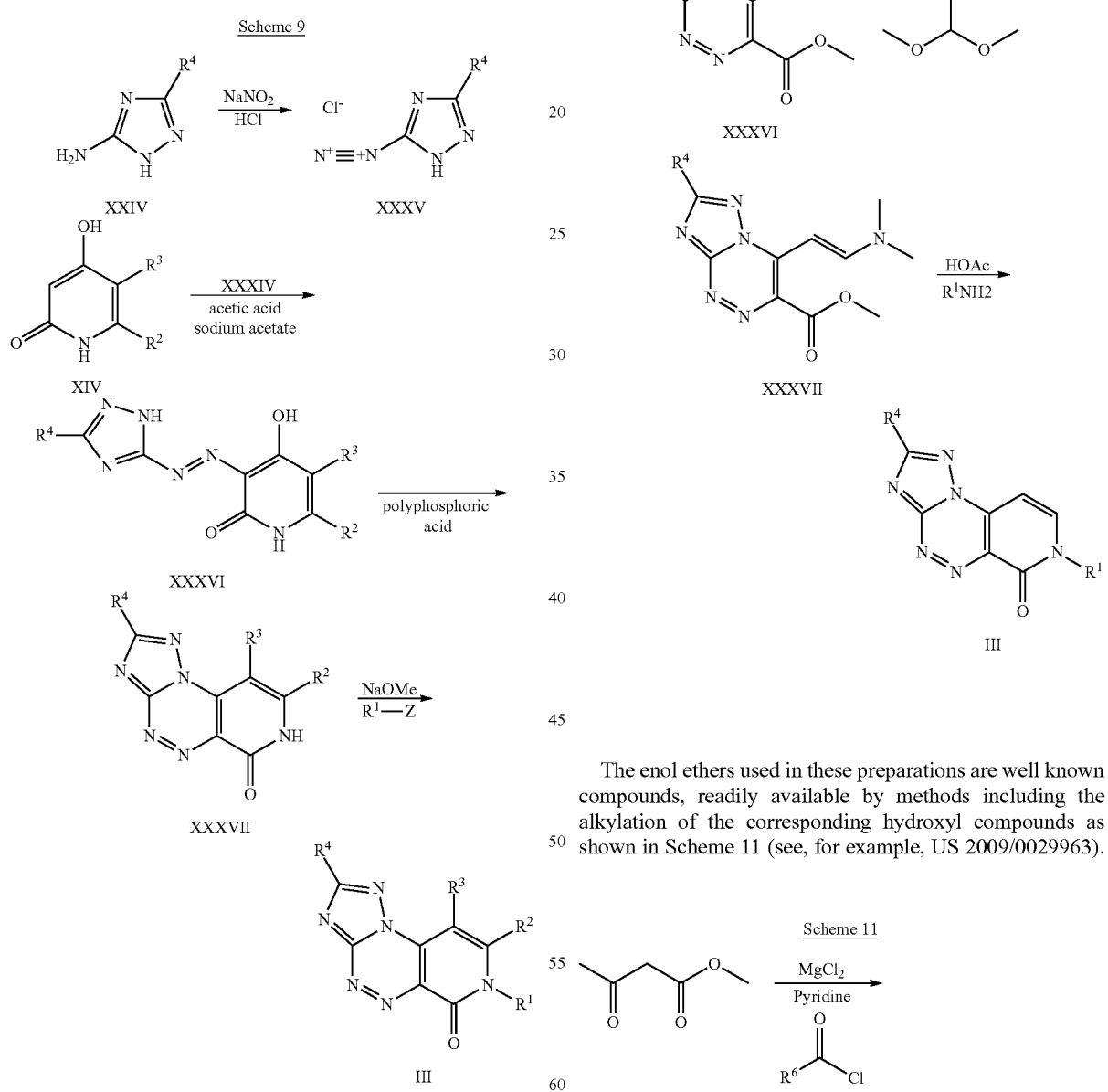

Scheme 10 shows an alternative synthesis of analogs of type III. In this approach, a triazole diazonium salt XXXV is treated with an enol ether XXVIII in warm DMF to give the fused heterocycle XXXVI. Compound XXXVI is in turn converted to final product III using methods similar to those described for the conversion of XXX to II.

The enol ethers used in these preparations are well known compounds, readily available by methods including the alkylation of the corresponding hydroxyl compounds as shown in Scheme 11 (see, for example, US 2009/0029963).

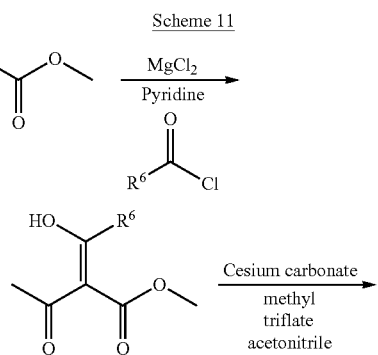

Synthesis of Compounds of Formula IV

Performing the synthetic route shown in Scheme 7 with aminotriazole XXIV in place of aminopyrazole VI gives IV as shown in Scheme 12.

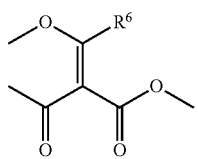

mL dimethylformamide with heating to reflux for two days. The solvent is evaporated and the product 16 is isolated by column chromatography on sililca gel. One half gram of this material is dissolved in 5 mL of dimethylformamide dimethyl acetal and treated with 0.25 g of dimethylformamide dimethyl acetal for 2 hours. The reaction mixture is partitioned between water and dichloromethane and the solvent was evaporated. The crude product 17 from this step is treated with 1-amino-3-(dimethyamino)propane in a 5 mL of 19:1 ethanol/acetic acid and refluxed for 12 hours. The final product 13 is isolated by chromatography.

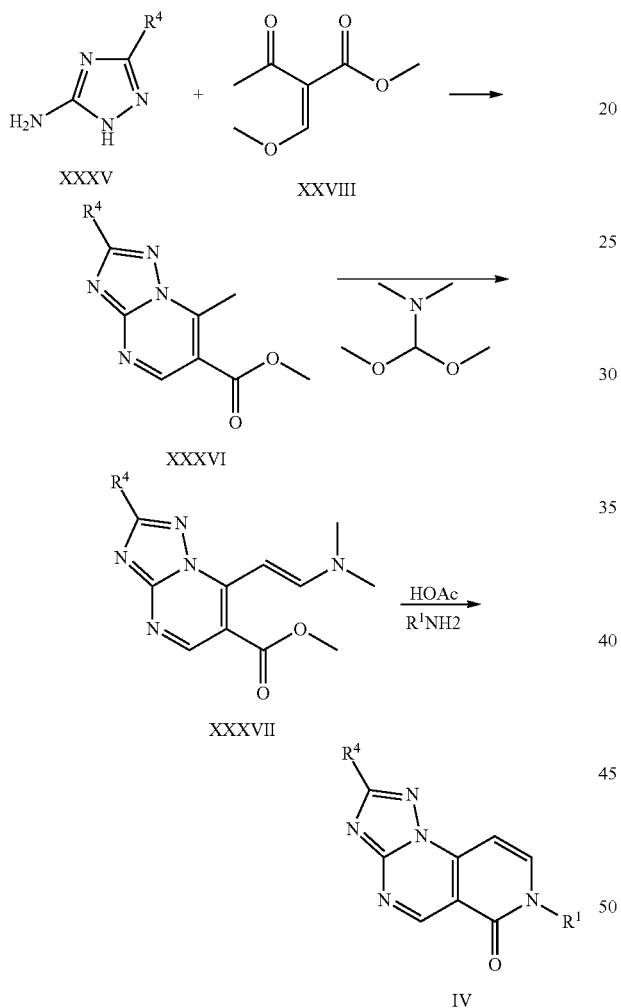

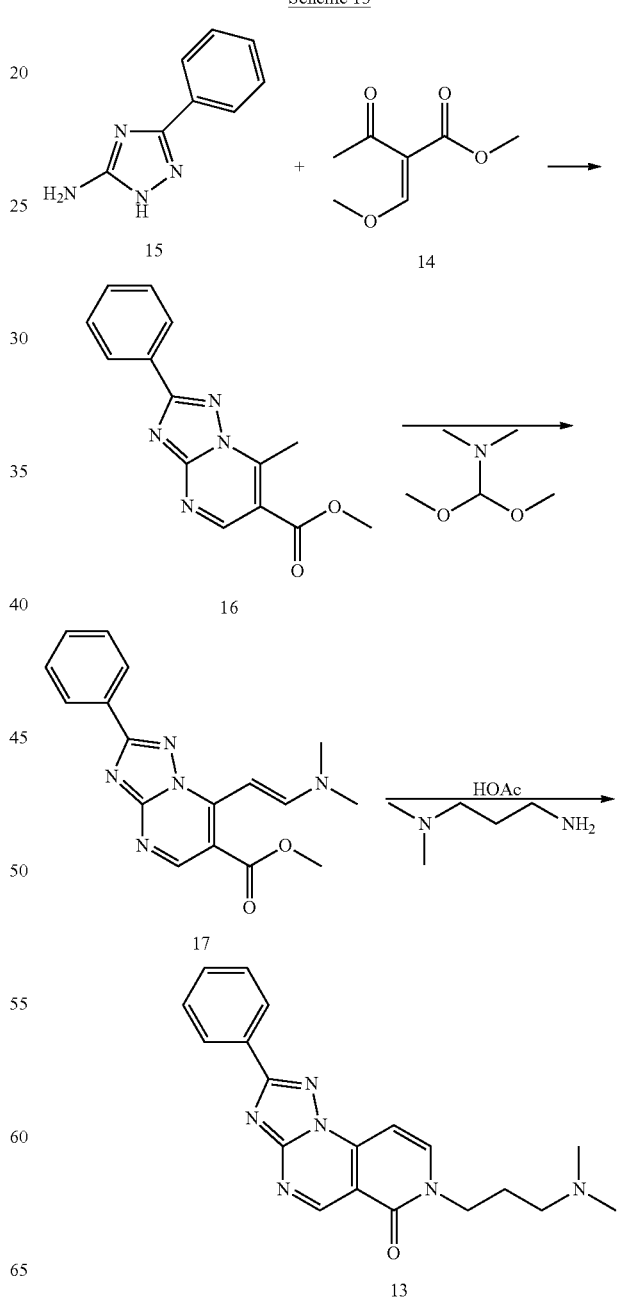

Compounds 1-13 described herein are commercially available from ChemBridge Corporation of San Diego, Calif.

EXAMPLES

Example 1

Synthesis of Compound 13

Commercially available 5-phenyl-1 H -[1,2,4]triazol-3-ylamine (1.0 g) and enol ether 14 (1.0 g) are combined in 5

Example 2

Synthesis of Compound 8

Compound 8 is prepared from 4-(p-chlorophenyl)-2H-pyrazol-3-ylamine using the same procedures used to prepare compound 8 from 18.

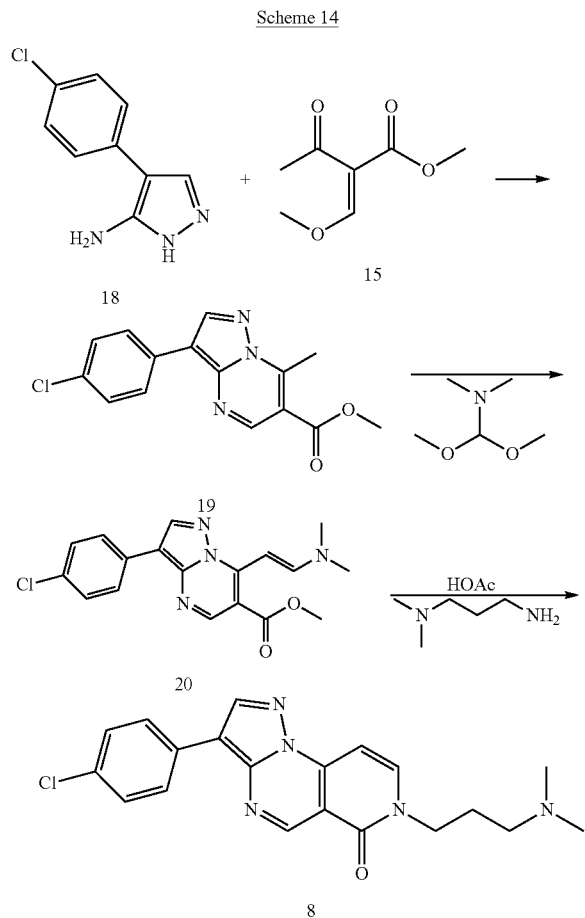

Example 3

Synthesis of Compound 1

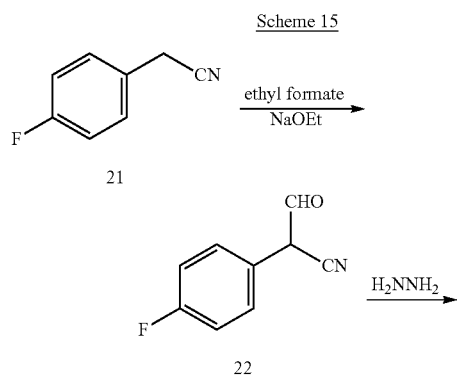

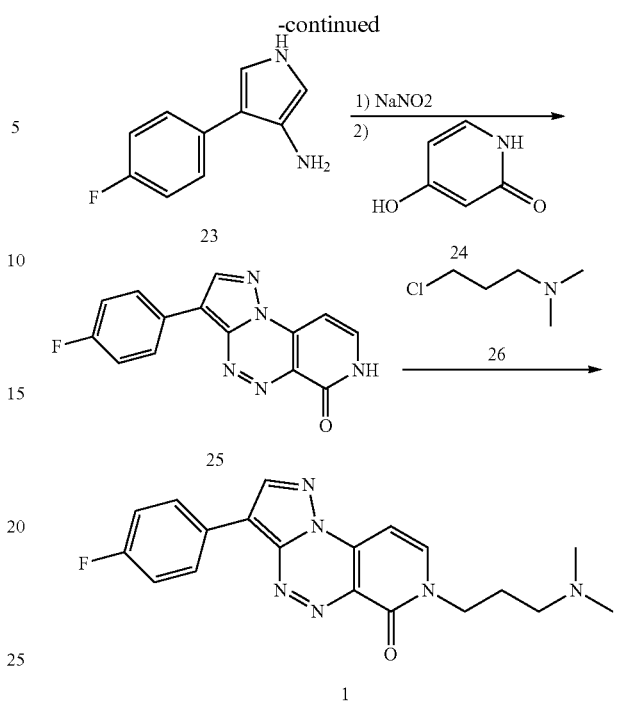

A fresh solution of sodium ethoxide was prepared by dissolution of sodium (2.73 g, 119 mmol) in ethanol (150 mL). The mixture was cooled to 0° C. and 4-fluorophenylacetonitrile (108 mmol) was added. The mixture was stirred for 5 min, followed by the addition of ethyl formate (20.0 g, 270 mmol). The reaction mixture was heated to reflux and stirred for 18 h, then cooled to room temperature, and concentrated in vacuo. The residue was diluted with water (100 mL), and the pH was adjusted to 3-4 using 1 N hydrochloric acid. The mixture was extracted with diethyl ether (3×100 mL). The combined organic layers were washed with brine (100 mL), dried over sodium sulfate, filtered, and concentrated to afford 22, which was used without further purification, yield 95%.

Hydrazine hydrate (10.8 g, 216 mmol) was added to a stirred solution of 22 (108 mmol) in ethanol (100 mL), followed by acetic acid (10 mL). The reaction mixture was heated at reflux for 2 h, then cooled to room temperature, concentrated in vacuo, and then diluted with water (100 mL) and diethyl ether (200 mL). The organic layer was separated, washed with water (100 mL) and brine (2×100 mL), dried over sodium sulfate, and concentrated to afford 23 (90%) as a dark orange oil, which was used without further purification, yield 90%.

A solution of 23 (5.19 g, 0.03 mol) in water (30 mL) and hydrochloric acid (9 mL) was cooled to 0° C. The mixture was treated with sodium nitrite (2.07 g, 0.03 mol) in water. The pre-cooled solution was added to 2,4-dihydroxypyridine 24 (0.03 mol) and sodium acetate (30 g, 0.37 mol) in acetic medium (30 mL). The reaction mixture was stirred at room temperature for 1 h and kept standing overnight. The solid deposit was collected by filtration and washed well with water. The crude compound 25 was recrystallized from acetic acid to afford 25 as a red solid, yield 70%.

A mixture of 25 (5 g, 17 mmol, 1 equiv), 3-chloro-N,N-dimethylpropan-1-amine hydrochloride (3.3 g, 21 mmol, 1.2 equiv) and K$_2$CO$_3$ (5.7 g, 41.6 mmol, 2.4 equiv in DMF, 50 mL) was heated at 80° C. for 16 h. Additional 3-chloro-N,N-dimethylpropan-1-amine hydrochloride (2.7 g, 17 mmol, 1.0 equiv) and $K_2CO_3$ (2.3 g, 17 mmol, 1.0 equiv), were added and the resulting mixture was heated at 80° C. for 8 h. The reaction mixture was then poured into water (50 mL) and extracted with ethyl acetate (3×50 mL). The combined organic layers were dried over sodium sulfate and concentrated. The residue was purified by flash column chromatography with $CH_2Cl_2$ in MeOH to afforded Compound 1 in 45% yield as a light brown solid.

Example 4

In Vitro Treatment with Compound 1 Induces Cholesterol Relocalization in NPC Fibroblasts Compound 1 was tested in vitro for its effect on cholesterol localization in NPC fibroblasts. The following experiments utilized Coriell GM18453 (I1061T/I1061T) cells which are immortalized cell lines prepared from NPC patient fibroblasts. These cells have a known deficiency in cholesterol esterification.

Compound 1 (FIG. 1B), U18666A (positive control, FIG. 1C), and DMSO (vehicle control, FIG. 1A) were individually dispensed into 96 well In Vitro Scientific glass bottom black walled plates using the Echo acoustic liquid handler for the final concentrations indicated. Cells were suspended in media (DMEM, 5% FBS, 1% P/S, 2 mM L-glutamine) and then added to each well at 1750 cells per well. The final concentration of Compound 1 and U11866A was 10 µM.

After a 48 hr incubation cells were fixed and stained with filipin using components from the Cholesterol Cell Based Detection Kit from Cayman. Filipin was used at a final concentration of 50 µg/mL. Cells were imaged using the ImageXpress from Molecular Devices and analyzed with MetaXpress. As shown in FIG. 1, both Compound I and the positive control, U18666A (FIGS. 1B and 1C, respectively), caused an increase in the amount of cytoplasmic free/unesterified cholesterol, relative to vehicle control (FIG. 1A), as visualized by an increase in filipin staining.

Figure 2:
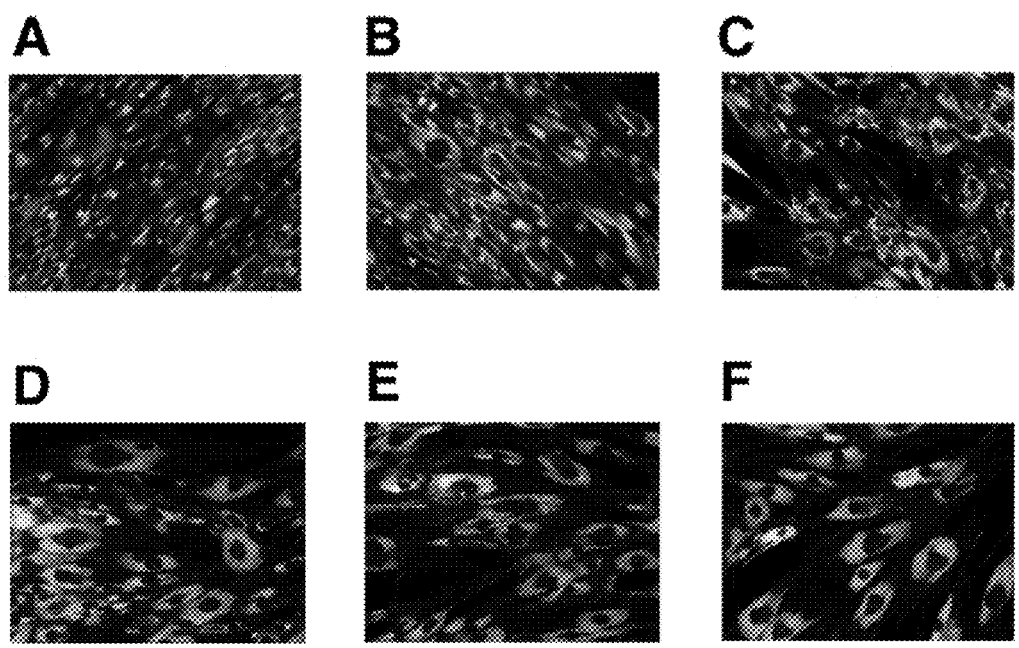
FIG. 2 is a time course of photomicrographs showing the binding of filipin to cholesterol in an NPC patient fibroblast cell line that was untreated (FIG. 2A) or treated with 10 μM Compound 1 and assayed every 24 hours for five days (FIG. 2B-F).

The experiment was repeated in GM18453 cells except that filipin staining was assessed in one set of wells every 24 hours for a total of five days. FIG. 2A provides an exemplary photomicrograph of a cells treated with vehicle control. There were no notable changes to the filipin staining of the vehicle-treated over the five day culture period, FIG. 2B-2F are representative photomicrographs of the Compound 1-treated cells after 1-5 days in culture, respectively. Increases in the amount of cytoplasmic free/unesterified cholesterol were observed after a 24 hour culture period and the effect was sustained throughout the five day study period.

Taken together, these data indicate that Compound 1 alters cellular cholesterol homeostasis by mobilizing cholesterol, thereby enabling cholesterol-dependent processes.

Example 5

In Vivo Treatment with Compound 1 Rescues A Nematode Model of NPC

This experiment tested the ability of Compound 1 to rescue NPC-1 null nematodes. A population of NPC1 null worms was scaled up on large petri plates (100 mm or 60 mm) to produce a large population of gravid adults. One day prior to assay, the adult worms were bleached to obtain all eggs. Eggs were allowed to hatch overnight in M9 by rocking tubes. On day of assay, the presence of L1 larvae was confirmed.

A lawn of HB101 bacteria were grown on NGM agar plates (4 ml). The plates were prepared either with or without exogenous cholesterol. Solutions of DMSO (vehicle control), 50 µM cyclodextrin, 50 µM suberoylanilide hydroxamic acid (SAHA), and 50 µM Compound 1 were prepared in 25% cremaphor, added to plates around the bacterial lawn, and allowed to dry. An additional set of plates prepared with 25% cremaphor alone was used as a second vehicle control.

Figure 3:
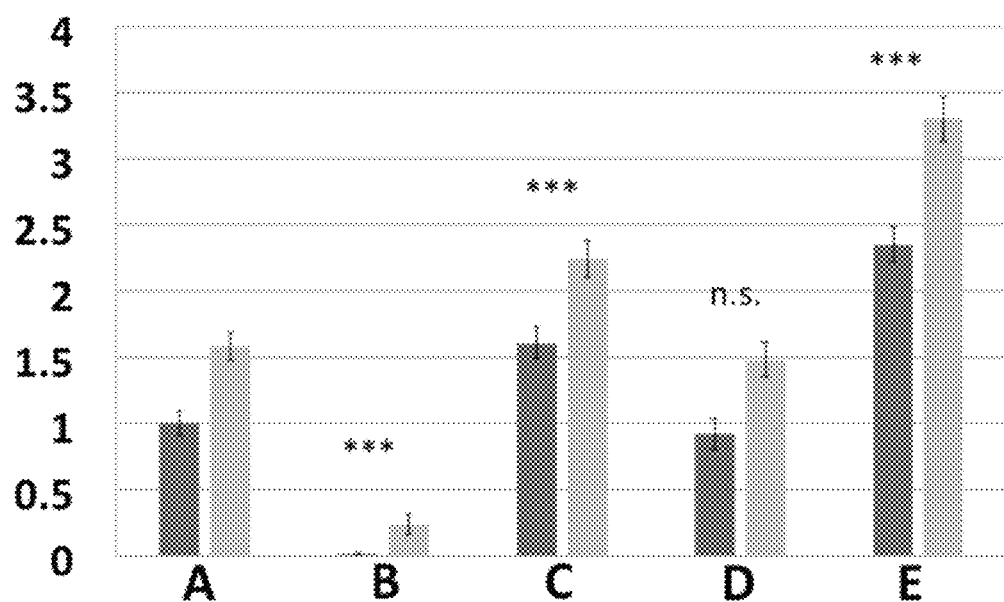
FIG. 3 is a bar graph showing the number of *C. elegans* eggs counted on Day 1 of adulthood in the presence (dark) or absence (light) of supplemental cholesterol and upon treatment with either DMSO (FIG. 3A), U18666A (FIG. 3B), 25 μM Compound 1 (FIG. 3C), SAHA (FIG. 3D), or 0.5% cyclodextrin (FIG. 3E).

Fifty to seventy L1 larvae were added to each plate and incubated at room temperature for two days. On day 3, L1 worms had matured into Day 1 adults bearing row of eggs. Eggs were counted microscopically and the average number of eggs per adult worm for each incubation condition was calculated. As shown in FIG. 3, treatment with either cyclodextrin (E, 0.5%) or Compound 1 (C, 25 µM) resulted in a statistically significant increase in the number of eggs per adult worm relative to treatment with either DMSO (A) control or SAHA (D, 50 µM). $p<0.001$ (***), relative to DMSO for the same cholesterol treatment, using Student's t-test. By contrast, treatment with U18666A (B, 75 µM), which causes NPC-like disease in both cell and animal models, significantly exacerbates the egg laying deficit of NPC null nematodes. There was no statistically significant difference between treatment with DMSO control in the 25% cremaphor carrier relative to the carrier alone (data not shown).

Taken together, these data indicate that Compound 1 and U18666A have opposite effects with respect to development and growth in the nematode NPC model, even though these two compounds appear to induce a similar cholesterol mobilization phenotype in NPC patient fibroblasts. Two-model authentication where one model is a genetically matched whole animal and the other model is a patient cell ensures that a hit compound with both cellular and organismal efficacy is selected in the primary screening campaign. Relying solely on a cellular phenotype without whole-organism context is deceiving and may in fact result in the discarding of other desirable hit compounds.

Example 6

Effects of Compound 1 on the Uptake, Transport, and Cellular Distribution of NBD-cholesterol For the NBD-cholesterol (Thermo Fisher, N1148) experiment, cells (Coriell, GM09503) were seeded in a 96 well plate with DMEM (10% FBS, PennStrep, and 2 mM L-glutamine). Cells adhered to the bottom of the plate for 24 hrs. Media was removed, and cells were washed 3× with 1×PBS and then serum starved for 2 days in DMEM containing 1% FBS. The duration and concentration of serum starvation can be varied. The NBD-cholesterol was taken from a stock of 1 mg/mL in ethanol. The aliquots can be stored for up to one year at −20° C. The cells were then incubated with a final concentration of 20 µg/mL of NBD-cholesterol in DMEM low serum. The cells were then fixed at various timepoints using 4% paraformaldehyde and washed 3× with 1×PBS prior to imaging. The cells can also be live imaged without fixation.

Figure 4:
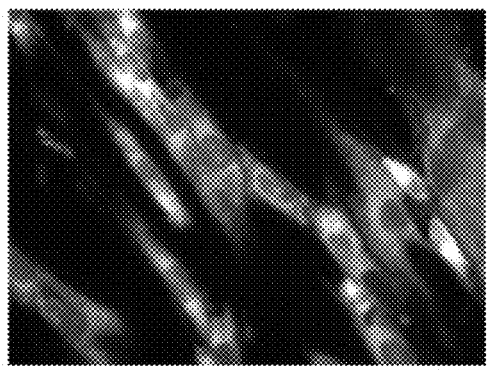
FIG. 4 shows the effects of Compound 1 (FIG. 4B) versus DMSO control (FIG. 4A) on the uptake, transport and cellular distribution of NBD-cholesterol, a fluorescent analog of cholesterol that is used as a probe in cell biology experiments.
Figure 4:
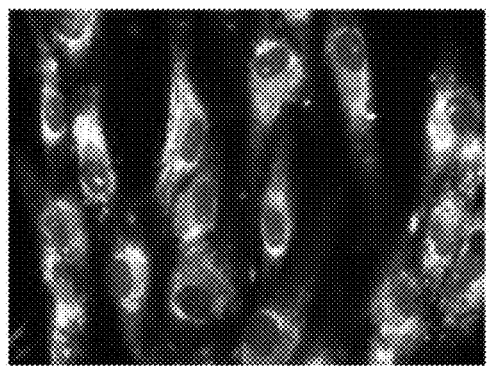

The results are summarized in FIG. 4. FIG. 4 shows the effects of Compound 1 (FIG. 4B) versus DMSO control (FIG. 4A) on the uptake, transport and cellular distribution of NBD-cholesterol.

Example 7

Effects of Compound 1 on Liver Biomarkers in A Mouse Model of NPC

Figure 5:
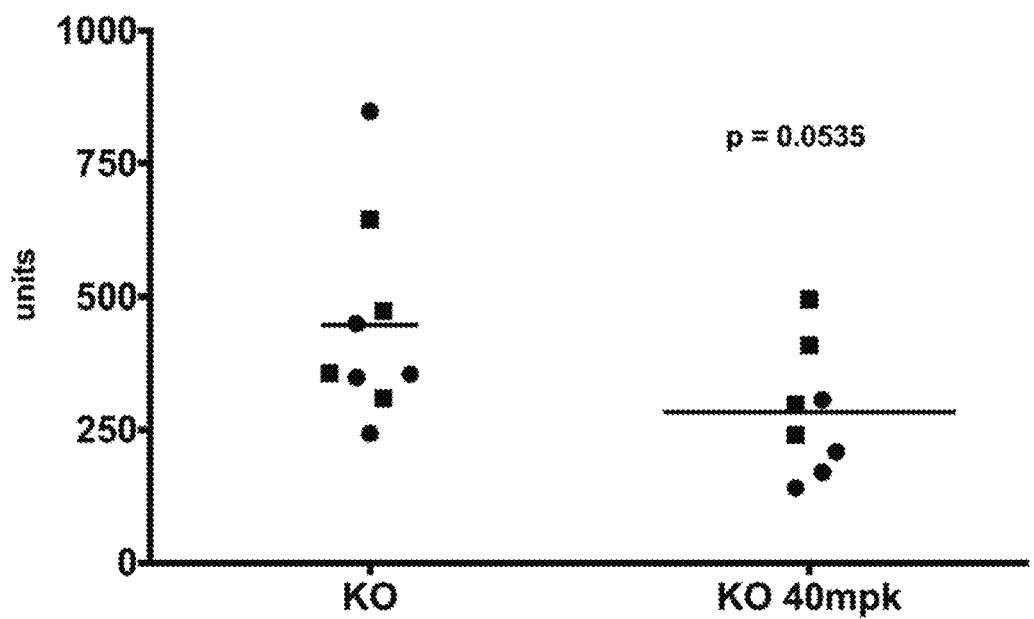
FIG. 5 shows the effects of Compound 1 on Alanine aminotransferase (ALT) blood levels in male (circles) and female (squares) NPC1 knockout mice. KO=NPC1 knockout mice treated with vehicle alone; KO 40 mpk=NPC1 knockout mice treated with 40 mg/kg of Compound 1. Lines represent the group mean.
Figure 6:
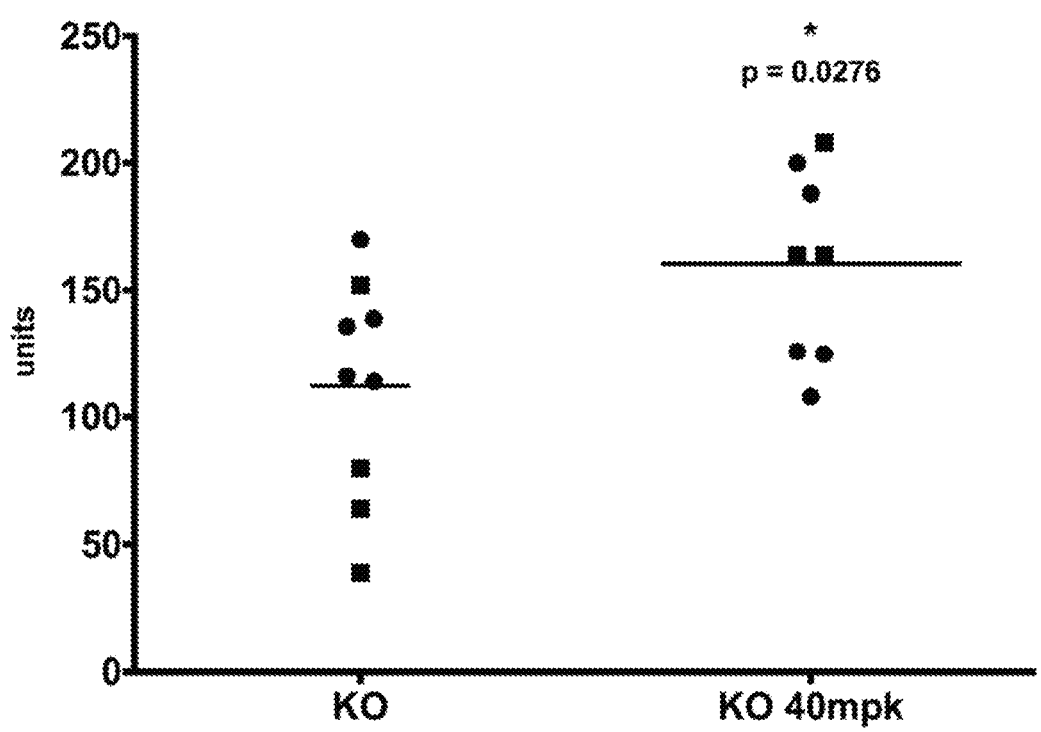
FIG. 6 shows the effects of Compound 1 on blood glucose levels in male (circles) and female (squares) NPC1 knockout mice. KO=NPC1 knockout mice treated with vehicle alone; KO 40 mpk=NPC1 knockout mice treated with 40 mg/kg of Compound 1. Lines represent the group mean.
Figure 7:
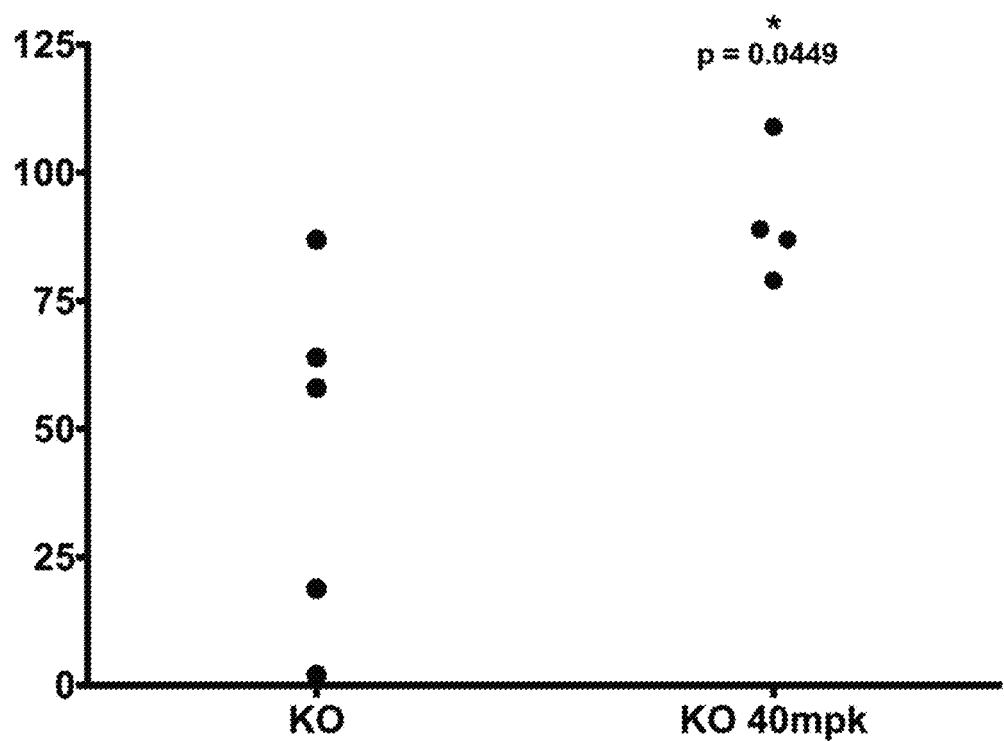
FIG. 7 shows the effects of Compound 1 on blood HDL cholesterol levels in male NPC1 knockout mice. KO=NPC1 knockout mice treated with vehicle alone; KO 40 mpk=NPC1 knockout mice treated with 40 mg/kg of Compound 1.

Day 35 NPC1 knockout Balb/c male and female mice were treated with Compound 1 by daily oral administration (p.o. q.d.) for 21 days and then sacrificed. Terminal blood draws were analyzed for alanine aminotransferase (FIG. 5), glucose (FIG. 6) and high-density lipoprotein cholesterol (FIG. 7). Using Student's t-test, comparison of alanine aminotransferase levels in NPC1 knockout mice treated with 40 mg/kg of Compound 1 to levels in NPC1 knockout mice treated with vehicle alone yielded a p value near significance (p=0.0535); comparison of glucose levels in NPC1 knockout mice treated with 40 mg/kg of Compound 1 to NPC1 knockout mice treated with vehicle alone yielded a significant p value (p=0.0276); and, finally, comparison of high-density lipoprotein cholesterol levels in NPC1 knockout mice treated with 40 mg/kg of Compound 1 to NPC1 knockout mice treated with vehicle alone yielded a significant p value (p=0.0449).

Taken together, the mechanism of action of Compound 1 appears to involve activation of a bypass pathway that rescues the lipid transport, cholesterol mobilization and autophagy defects caused by loss of NPC1 gene function in nematode, cellular and mouse models of NPC disease.

What is claimed is:

1. A method for treating a lysosomal storage disorder in a subject in need thereof comprising administering to the subject a therapeutically effective amount of a pharmaceutical formulation comprising a pharmaceutically acceptable excipient and a compound of Formula I:

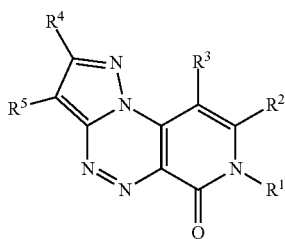

I or a pharmaceutically acceptable salt thereof, wherein:

$R^1$ is $-(C_2\text{-}C_6 \text{ alkylidene})\text{-NR}^6R^7$, $-(C_2\text{-}C_6 \text{ alkylidene})\text{-}X^1\text{-}(C_2\text{-}C_6 \text{ alkylidene})\text{-NR}^6R^7$, or $-(C_3\text{-}C_6 \text{ cycloalkylidene})\text{-NR}^6R^7$, each of which is optionally substituted with one or more groups independently selected from $C_1\text{-}C_6$ alkyl, $C_3\text{-}C_6$ cycloalkyl, halogen, —OH, alkoxy, —NO$_2$, amino, —CN, —COOH, —COOR$^8$, and amido;

$R^2$, $R^3$, $R^4$, and $R^5$ are independently selected from H, halogen, —CN, amino, —NO$_2$, $C_1\text{-}C_6$ alkyl, $C_3\text{-}C_6$ cycloalkyl, alkoxy, $-(C_1\text{-}C_6 \text{ alkylidene})\text{-}X^2\text{-}(C_1\text{-}C_6 \text{ alkyl})$, aryl, heterocyclyl, heteroaryl, aralkyl, heteroarylalkyl, and heterocyclylalkyl, wherein the amino, $C_1\text{-}C_6$ alkyl, $C_3\text{-}C_6$ cycloalkyl, alkoxy, $-(C_1\text{-}C_6 \text{ alkylidene})\text{-}X^2\text{-}(C_1\text{-}C_6 \text{ alkyl})$, aryl, heterocyclyl, heteroaryl, aralkyl, heteroarylalkyl, and heterocyclylalkyl are optionally substituted with one or more groups independently selected from $C_1\text{-}C_6$ alkyl, $C_3\text{-}C_6$ cycloalkyl, halogen, —OH, -alkoxy, —NO$_2$, amino, —CN, —COOH, —COOR$^9$, and amido;

$X^1$ and $X^2$ are independently selected from null, —O—, —S—, —SO$_2$—, —(C=O)—, —N(R$^{11}$)—, and —C(O)N(R$^{12}$)—;

$R^6$ and $R^7$ are independently selected from H, $C_1\text{-}C_6$ alkyl, and $C_3\text{-}C_6$ cycloalkyl; or $R^6$, $R^7$, and the nitrogen to which they are attached join together to form a heterocyclic ring;

$R^8$ and $R^9$ are independently selected from H, $C_1\text{-}C_6$ alkyl, and $C_3\text{-}C_6$ cycloalkyl; and $R^{11}$ and $R^{12}$ are independently selected from H, $C_1\text{-}C_6$ alkyl, and $C_3\text{-}C_6$ cycloalkyl, wherein the $C_1\text{-}C_6$ alkyl and $C_3\text{-}C_6$ cycloalkyl are optionally substituted with one or more groups independently selected from halogen, —OH, amino, alkoxy, —CN, and —NO$_2$;

and wherein the lysosomal storage disorder is Niemann Pick type A disease, Niemann Pick type C disease, Gaucher type 1 disease, or Gaucher type 2 disease.

2. The method of claim 1, wherein the method further comprises administering to the subject a therapeutically effective amount of cyclodextrin.

3. The method of claim 1, wherein the lysosomal storage disorder is Niemann Pick type C disease.

* * * * *